United States Patent
Kim et al.

(10) Patent No.: US 10,130,712 B2
(45) Date of Patent: Nov. 20, 2018

(54) ***CORYNEBACTERIUM* SP. BACTERIA AND MINICELL DERIVED THEREFROM, AND USE THEREOF**

(71) Applicant: INDUSTRY FOUNDATION OF CHONNAM NATIONAL UNIVERSITY, Gwangju (KR)

(72) Inventors: Geun Joong Kim, Gwangju (KR); Jin-Young Lee, Gwangju (KR); Sa-Young Min, Gwangju (KR); Sung-Hwan You, Gwangju (KR); Jung-Joon Min, Gwangju (KR)

(73) Assignee: INDUSTRY FOUNDATION OF CHONNAM NATIONAL UNIVERSITY, Gwangju (KR)

( * ) Notice: Subject to any disclaimer, the term of this patent is extended or adjusted under 35 U.S.C. 154(b) by 0 days.

(21) Appl. No.: 15/023,245

(22) PCT Filed: Oct. 21, 2015

(86) PCT No.: PCT/KR2015/011154
§ 371 (c)(1),
(2) Date: Mar. 18, 2016

(87) PCT Pub. No.: WO2016/140419
PCT Pub. Date: Sep. 9, 2016

(65) Prior Publication Data
US 2017/0354738 A1     Dec. 14, 2017

(30) Foreign Application Priority Data
Mar. 4, 2015   (KR) .................... 10-2015-0030224

(51) Int. Cl.
*A61K 47/00* (2006.01)
*A61K 47/46* (2006.01)
*A61K 38/50* (2006.01)
*C12R 1/15* (2006.01)
*A61K 35/74* (2015.01)
*A61K 47/69* (2017.01)

(52) U.S. Cl.
CPC .............. *A61K 47/46* (2013.01); *A61K 35/74* (2013.01); *A61K 38/50* (2013.01); *A61K 47/6901* (2017.08); *C12R 1/15* (2013.01); *C12Y 305/01001* (2013.01); *Y02A 50/473* (2018.01); *Y02A 50/481* (2018.01)

(58) Field of Classification Search
None
See application file for complete search history.

(56) References Cited

U.S. PATENT DOCUMENTS

2003/0198996 A1   10/2003   Surber et al.
2014/0220116 A1   8/2014    Brahmbhatt et al.
2016/0095941 A1*  4/2016    Brahmbhatt ..... A61K 47/48815
                                                    424/450

FOREIGN PATENT DOCUMENTS

KR   10-2014-0112888 A   9/2014

OTHER PUBLICATIONS

Song et al. 2011 (Engineered Corynebacterium glutamicum as an endotoxin-free platform strain for lactate-based polyester production; Appl. Microbiol Biotechnol. DOI 10.1007/s00253-011-3718-0; pp. 1-9). (Year: 2011).*
MacDiarmid et al. 2009 (Sequential treatment of drug-resistant tumors with targeted minicell containing siRNA or a cytotoxic drug; Nature Biotechnology 27(7):643) (Year: 2009).*
Lee et al. 2015 (Generation of Minicells from an Endotoxin-Free Gram-Positive Strain Corynebacterium glutamicum; J. Microbiol. Biotechnol. 25(4): 554-558) (Year: 2015).*
Huang SL, Liposomes in ultrasonic drug and gene delivery, Advanced Drug Delivery Review, 60:1167-1176, 2008.
Kim SH, et al., Structural modifications of outer membrane vesicles to refine them as vaccine delivery vehicles, Biochimica et Biophysica Acta, 1788:2150-2159, 2009.
Savic R, el al., Micellar Nanocontainers Distribute to Defined Cytoplasmic Organelles, Science, 300:615-618, 2003.
Torchilin VP., Multifunctional nanocarriers, Advanced Drug Delivery Review, 64:302-315, 2012.
MacDiarmid JA, et al., Bacterially Derived 400 nm Particles for Encapsulation and Cancer Cell Targeting of Chemotherapeutics, Cancer Cell, 11:431-445, 2007.
MacDiarmid JA et al., Sequential treatment of drug-resistant tumors with targeted minicells containing siRNA or a cytotoxic drug, Nat Biotechnol., 27:643-651, 2009.
Nakayama K et al., Microbial Production of Essential Amino Acids With Corynebacterium Glutamicum Mutants, Adv. Exp. Med. Biol., 105:649-661, 1978.

(Continued)

*Primary Examiner* — Mary Maille Lyons
(74) *Attorney, Agent, or Firm* — The PL Law Group, PLLC

(57) ABSTRACT

A drug delivery system composition includes *Corynebacterium* sp. bacteria or *Corynebacterium* sp. bacteria-derived minicells. The drug delivery system composition is safer for use in human bodies than other bacteria (for example, *Escherichia coli* (*E. coli*), *Salmonella* sp. bacteria, *Bacillus* sp. bacteria, or the like), or other bacteria-derived drug delivery system. When an anti-cancer drug protein expression construct (protein expression recombinant vector or the like) is included, over-expression of an anti-cancer drug protein, effective protein expression control in vivo, and targeting technique using expression of targeting factor. The drug delivery system composition enables stable drug delivery in vivo, thereby maximizing anti-cancer therapeutic effects.

16 Claims, 9 Drawing Sheets
Specification includes a Sequence Listing.

(56) References Cited

OTHER PUBLICATIONS

Schafer A, et al., Small mobilizable multi-purpose cloning vectors derived from the *Escherichia coli* plasmids pK18 and pK19: selection of defined deletions in the chromosome of Corynebacterium glutumicum, Gene, 145:69-73, 1994.
Date M et al., Secretion of human epidermal growth factor by Corynebacterium glutamicum, Lett. Appl. Microbiol., 42:66-70, 2006.
Michal et al., Cell growth and cell division in the rod-shaped actinomycete Corynebacterium glutamicum, Antonie van Leeuwenhoek, 94:99-109, 2008.
Ebersbach H, et al. Affilin—Novel Binding Molecules Based on Human γ-B-Crystallin, an All β-Sheet Protein, J. Mol. Biol., 372:172-185, 2007.
Johnson A, et al. Sensitive Affimer and Antibody Based Impedimetric Label-Free Assays for C-Reactive Protein, Anal. Chem., 7;84:6553-6560, 2012.
Krehenbrink M, et al., Artificial Binding Proteins (Affitins) as Probes for Conformational Changes in Secretin PuID, J. Mol. Biol., 383:1058-1068(2008).
Skerra A, et al., Alternative binding proteins: Anticalins—harnessing the structural plasticity of the lipocalin ligand pocket to engineer novel binding activities, FEBS J., 275:2677-2683, 2008.
Silverman J, et al., Multivalent avimer proteins evolved by exon shuffling of a family of human receptor domains, Nat. Biotechnol., 23:1556-1561, 2005.
Koide A, et al., Antibody Mimics Based on the Scaffold of the Fibronectin Type III Domain, Methods Mol. Biol., 352:95-109, 2007.
van der Rest ME, et al., A heat shock following electroporation induces highly ef®cient transformation of Corynebacterium glutamicum with xenogeneic plasmid DNA, Appl. Microbiol. Biotechnol., 52:541-545, 1999.
A Burkovski et al., Cell Envelope of Corynebacteria: Structure and Influence on Pathogenicity, ISRN Microbiol. 2013:11, 2013.
W Yao et al., Display of alpha-amylase on the surface of Corynebacterium glutamicum cells by using NCgl1221 as the anchoring protein, and production of glutamate from starch, Arch. Microbiol., 191:751-759, 2009.
WD Schubert et al., Structure of Internalin, a Major Invasion Protein of Listeria monocytogenes, in Complex with Its Human Receptor E-Cadherin, Cell 111:825-836, 2002.
J Lee et al, Development and Characterization of Expression Vectors for Corynebacterium glutamicum, J. Microbiol. Biotechnol., 24:70-79, 2014.
K Subik et al., The Expression Patterns of ER, PR, HER2, CK5/6, EGFR, Ki-67 and AR by Immunohistochemical Analysis in Breast Cancer Cell Lines, Breast Cancer, 4:35-41, 2010.
MZ Li et al., Harnessing homologous recombination in vitro to generate recombinant DNA via SLIC, Nat. Methods., 4(3):251-6, 2007.
Vinh et al., Study on Minicell Generation of Lactobacillus acidophilus VTCC-B-871 for Drug Delivery, Journal of Applied Pharmaceutical Science vol. 3 (05), pp. 033-036, May 2013.
Yuyang Song et al., Engineered Corynebacterium glutamicum as an endotoxin-free platform strain for lactate-based polyester production, Appl Microbiol Biotechnol, 93:1917-1925, 2012.
Emmanouil D Karagiannis et al., Minicells overcome tumor drug-resistance, Nature Biotechnology, 27:620-621, 2009.

\* cited by examiner

A. surface expression constructs using auto-transporter (NCgl1221)
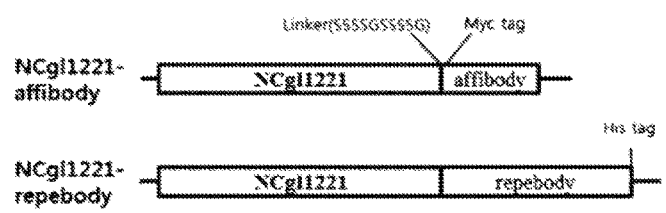
B. sortase-dependent surface expression constructs
• basic structure for sortase-dependent surface expression proteins
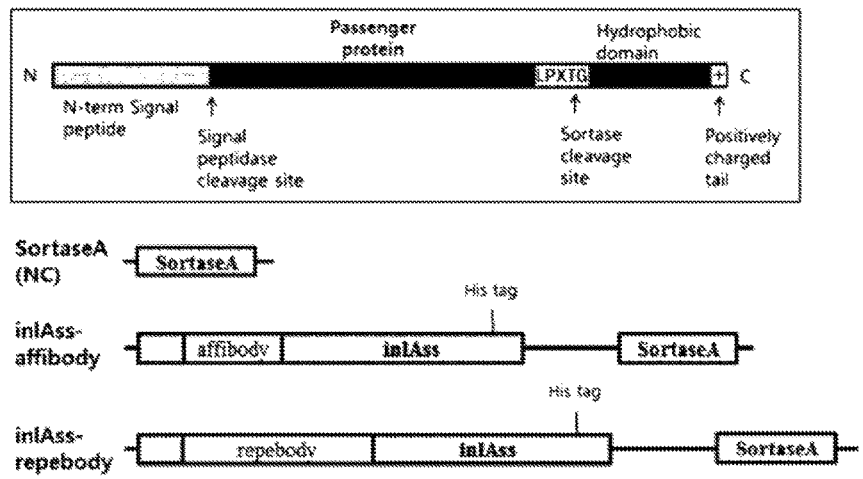
Fig. 3

A. surface expression results obtained using auto-transporter (NCgl1221)
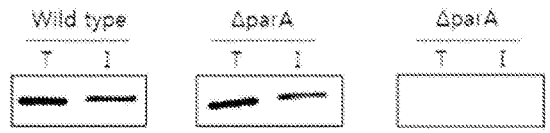
B. sortase-dependent surface expression results
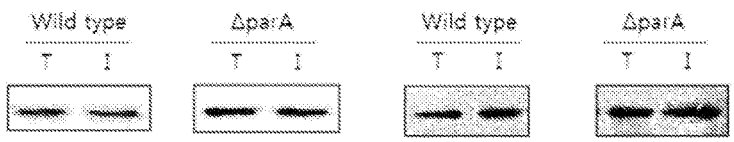
*T : Total I : Insoluble
Fig. 4
Confirming of specificity of affinity ligand surface expression minicells
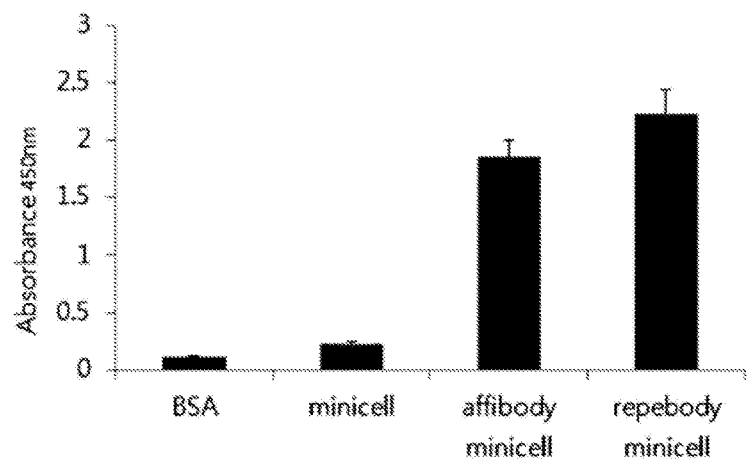
Fig. 5

- asparaginase (36.8 kDa)
1. w/o IPTG induction
2. w IPTG induction (3h)
3. w IPTG induction (4h)
4. w IPTG induction (6h)
- il32β (21.7 kDa)
- il32γ (26.6 kDa)
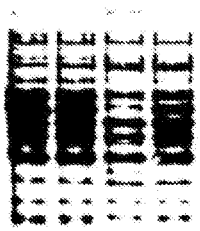
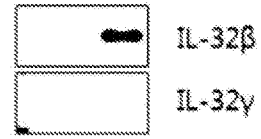
1. w/o IPTG induction
2. w IPTG induction (5h)
3. w IPTG induction (10h)
4. w IPTG induction (15h)
Fig. 7

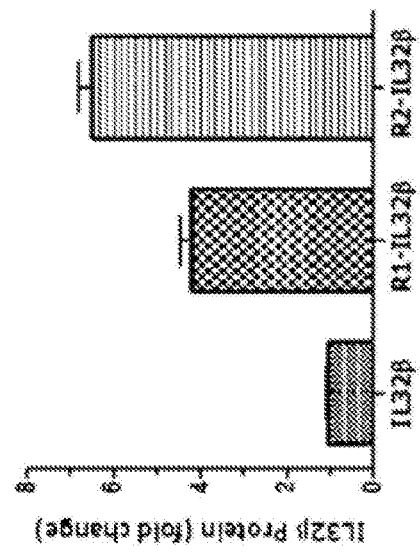
A. expression comparison after ramp-tag is applied to IL32β   B. expression comparison after ramp-tag is applied to IL32γ
Fig. 8

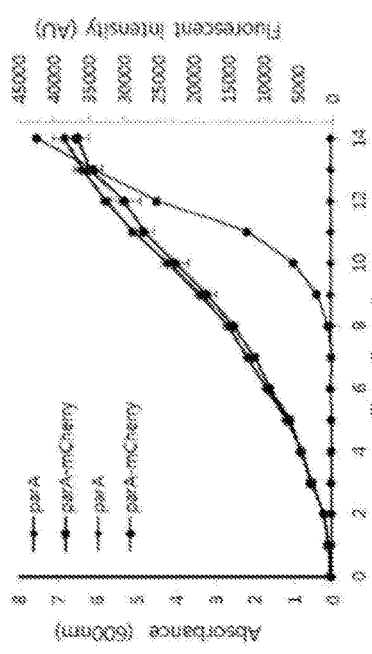
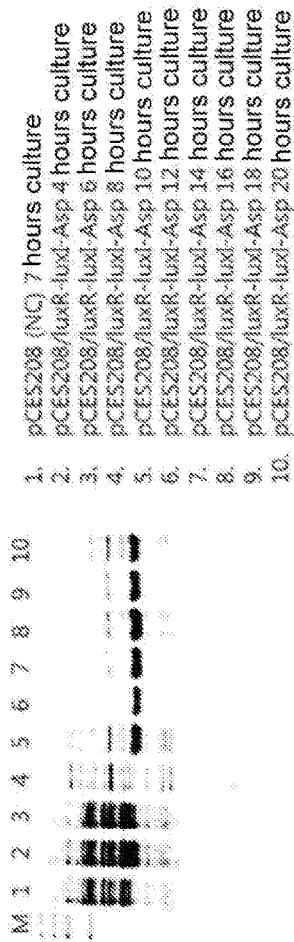

A. change in absorbance with respect to luxR-luxI-mCherry growth and quorum sensing-induced mCherry expression B. expression of asparaginase in luxR-luxI-asparaginase recombinant strain by quorum sensing 1. pCES208 (NC) 7 hours culture
2. pCES208/luxR-luxI-Asp 4 hours culture
3. pCES208/luxR-luxI-Asp 6 hours culture
4. pCES208/luxR-luxI-Asp 8 hours culture
5. pCES208/luxR-luxI-Asp 10 hours culture
6. pCES208/luxR-luxI-Asp 12 hours culture
7. pCES208/luxR-luxI-Asp 14 hours culture
8. pCES208/luxR-luxI-Asp 16 hours culture
9. pCES208/luxR-luxI-Asp 18 hours culture
10. pCES208/luxR-luxI-Asp 20 hours culture

Fig. 9

```
                        SEQUENCE LISTING

<160> NUMBER OF SEQ ID NOS: 48

<210> SEQ ID NO 1
<211> LENGTH: 23
<212> TYPE: DNA
<213> ORGANISM: Artificial Sequence
<220> FEATURE:
<223> OTHER INFORMATION: primer

<400> SEQUENCE: 1
ataagcttcg gctgcatgag gcc                                              23

<210> SEQ ID NO 2
<211> LENGTH: 33
<212> TYPE: DNA
<213> ORGANISM: Artificial Sequence
<220> FEATURE:
<223> OTHER INFORMATION: primer

<400> SEQUENCE: 2
cgtcgcagta aacttctttg aatacgttaa ttg                                   33

<210> SEQ ID NO 3
<211> LENGTH: 25
<212> TYPE: DNA
<213> ORGANISM: Artificial Sequence
<220> FEATURE:
<223> OTHER INFORMATION: primer

<400> SEQUENCE: 3
tactgcgacg tcaaccatcc ctatc                                            25

<210> SEQ ID NO 4
<211> LENGTH: 28
<212> TYPE: DNA
<213> ORGANISM: Artificial Sequence
<220> FEATURE:
<223> OTHER INFORMATION: primer

<400> SEQUENCE: 4
ataggatcca cgcccagatc tcaacatc                                         28

<210> SEQ ID NO 5
<211> LENGTH: 17
<212> TYPE: DNA
<213> ORGANISM: Artificial Sequence
<220> FEATURE:
<223> OTHER INFORMATION: primer
```

```
<400> SEQUENCE: 5
caatcgccgg gataacc                                                  17

<210> SEQ ID NO 6
<211> LENGTH: 23
<212> TYPE: DNA
<213> ORGANISM: Artificial Sequence
<220> FEATURE:
<223> OTHER INFORMATION: primer

<400> SEQUENCE: 6
attctaaact gtggtgtcat cgg                                           23

<210> SEQ ID NO 7
<211> LENGTH: 30
<212> TYPE: DNA
<213> ORGANISM: Artificial Sequence
<220> FEATURE:
<223> OTHER INFORMATION: primer

<400> SEQUENCE: 7
atggatccat tgagcttcgt aattaacggg                                    30

<210> SEQ ID NO 8
<211> LENGTH: 25
<212> TYPE: DNA
<213> ORGANISM: Artificial Sequence
<220> FEATURE:
<223> OTHER INFORMATION: primer

<400> SEQUENCE: 8
acaacattta acaaatttcg gcgcg                                         25

<210> SEQ ID NO 9
<211> LENGTH: 28
<212> TYPE: DNA
<213> ORGANISM: Artificial Sequence
<220> FEATURE:
<223> OTHER INFORMATION: primer

<400> SEQUENCE: 9
taaatgttgt ttttctaaaa accacgcc                                      28

<210> SEQ ID NO 10
<211> LENGTH: 30
<212> TYPE: DNA
<213> ORGANISM: Artificial Sequence
<220> FEATURE:
<223> OTHER INFORMATION: primer

<400> SEQUENCE: 10
ataagcttca attcgagatc atcttcatcg                                    30

<210> SEQ ID NO 11
<211> LENGTH: 19
<212> TYPE: DNA
<213> ORGANISM: Artificial Sequence
<220> FEATURE:
<223> OTHER INFORMATION: primer

<400> SEQUENCE: 11
cagatggcgg gaattctcg                                                19

<210> SEQ ID NO 12
<211> LENGTH: 14
```

<212> TYPE: DNA
<213> ORGANISM: Artificial Sequence
<220> FEATURE:
<223> OTHER INFORMATION: primer

<400> SEQUENCE: 12
agacagcgcg cggg                                                         14

<210> SEQ ID NO 13
<211> LENGTH: 32
<212> TYPE: DNA
<213> ORGANISM: Artificial Sequence
<220> FEATURE:
<223> OTHER INFORMATION: primer

<400> SEQUENCE: 13
ataagcttta tttacatttt ctgaaagacc gg                                     32

<210> SEQ ID NO 14
<211> LENGTH: 24
<212> TYPE: DNA
<213> ORGANISM: Artificial Sequence
<220> FEATURE:
<223> OTHER INFORMATION: primer

<400> SEQUENCE: 14
gatactatcg gtccaagaga cgcc                                              24

<210> SEQ ID NO 15
<211> LENGTH: 34
<212> TYPE: DNA
<213> ORGANISM: Artificial Sequence
<220> FEATURE:
<223> OTHER INFORMATION: primer

<400> SEQUENCE: 15
cgatagtatc gatagtagtc ccaagttttg atac                                   34

<210> SEQ ID NO 16
<211> LENGTH: 30
<212> TYPE: DNA
<213> ORGANISM: Artificial Sequence
<220> FEATURE:
<223> OTHER INFORMATION: primer

<400> SEQUENCE: 16
atcccgggga aaaagtagcc cggttctttg                                        30

<210> SEQ ID NO 17
<211> LENGTH: 22
<212> TYPE: DNA
<213> ORGANISM: Artificial Sequence
<220> FEATURE:
<223> OTHER INFORMATION: primer

<400> SEQUENCE: 17
cagagaattt agcaatgcag cg                                                22

<210> SEQ ID NO 18
<211> LENGTH: 19
<212> TYPE: DNA
<213> ORGANISM: Artificial Sequence
<220> FEATURE:
<223> OTHER INFORMATION: primer

<400> SEQUENCE: 18

-continued cacccatggc tgatttcaa                                          19

<210> SEQ ID NO 19
<211> LENGTH: 27
<212> TYPE: DNA
<213> ORGANISM: Artificial Sequence
<220> FEATURE:
<223> OTHER INFORMATION: primer

<400> SEQUENCE: 19
aaaaagccta tgattttagg cgtaccc                                 27

<210> SEQ ID NO 20
<211> LENGTH: 29
<212> TYPE: DNA
<213> ORGANISM: Artificial Sequence
<220> FEATURE:
<223> OTHER INFORMATION: primer

<400> SEQUENCE: 20
aaaggtacct tccacagtca tgaccttaa                               29

<210> SEQ ID NO 21
<211> LENGTH: 23
<212> TYPE: DNA
<213> ORGANISM: Artificial Sequence
<220> FEATURE:
<223> OTHER INFORMATION: primer

<400> SEQUENCE: 21
tttggtacct cttcctcatc ggg                                     23

<210> SEQ ID NO 22
<211> LENGTH: 24
<212> TYPE: DNA
<213> ORGANISM: Artificial Sequence
<220> FEATURE:
<223> OTHER INFORMATION: primer

<400> SEQUENCE: 22
tcggagctct cattttggtc gttg                                    24

<210> SEQ ID NO 23
<211> LENGTH: 27
<212> TYPE: DNA
<213> ORGANISM: Artificial Sequence
<220> FEATURE:
<223> OTHER INFORMATION: primer

<400> SEQUENCE: 23
ttaggtacca tggaaaccat taccgtg                                 27

<210> SEQ ID NO 24
<211> LENGTH: 25
<212> TYPE: DNA
<213> ORGANISM: Artificial Sequence
<220> FEATURE:
<223> OTHER INFORMATION: primer

<400> SEQUENCE: 24
aaagagctcg ctttgttagc agccg                                   25

<210> SEQ ID NO 25
<211> LENGTH: 33
<212> TYPE: DNA
<213> ORGANISM: Artificial Sequence -continued
<220> FEATURE:
<223> OTHER INFORMATION: primer

<400> SEQUENCE: 25
ttagatatcg ggaaaactct ttttgatagt aac    33

<210> SEQ ID NO 26
<211> LENGTH: 32
<212> TYPE: DNA
<213> ORGANISM: Artificial Sequence
<220> FEATURE:
<223> OTHER INFORMATION: primer

<400> SEQUENCE: 26
ccagatatcg gatggtaatg agaaattatt gc    32

<210> SEQ ID NO 27
<211> LENGTH: 33
<212> TYPE: DNA
<213> ORGANISM: Artificial Sequence
<220> FEATURE:
<223> OTHER INFORMATION: primer

<400> SEQUENCE: 27
taaggatcca tgagaaaaaa acgatatgta tgg    33

<210> SEQ ID NO 28
<211> LENGTH: 30
<212> TYPE: DNA
<213> ORGANISM: Artificial Sequence
<220> FEATURE:
<223> OTHER INFORMATION: primer

<400> SEQUENCE: 28
ttactgcagc tatttactag cacgtgcttt    30

<210> SEQ ID NO 29
<211> LENGTH: 44
<212> TYPE: DNA
<213> ORGANISM: Artificial Sequence
<220> FEATURE:
<223> OTHER INFORMATION: primer

<400> SEQUENCE: 29
tgatggtgat ggtgatgcat ttttgaatta taagggtcat aagc    44

<210> SEQ ID NO 30
<211> LENGTH: 39
<212> TYPE: DNA
<213> ORGANISM: Artificial Sequence
<220> FEATURE:
<223> OTHER INFORMATION: primer

<400> SEQUENCE: 30
atgcatcacc atcaccatca cgaagcttca ctccctaca    39

<210> SEQ ID NO 31
<211> LENGTH: 30
<212> TYPE: DNA
<213> ORGANISM: Artificial Sequence
<220> FEATURE:
<223> OTHER INFORMATION: primer

<400> SEQUENCE: 31
aaagtcgaca acttggtcta gatctgtttg    30

<210> SEQ ID NO 32
<211> LENGTH: 27
<212> TYPE: DNA
<213> ORGANISM: Artificial Sequence
<220> FEATURE:
<223> OTHER INFORMATION: primer

<400> SEQUENCE: 32
aaagtcgacc ccgtaaaaga aggtcac                                        27

<210> SEQ ID NO 33
<211> LENGTH: 32
<212> TYPE: DNA
<213> ORGANISM: Artificial Sequence
<220> FEATURE:
<223> OTHER INFORMATION: primer

<400> SEQUENCE: 33
aaagtcgaca acaaattcaa caaagaaatg ag                                  32

<210> SEQ ID NO 34
<211> LENGTH: 27
<212> TYPE: DNA
<213> ORGANISM: Artificial Sequence
<220> FEATURE:
<223> OTHER INFORMATION: primer

<400> SEQUENCE: 34
aaagtcgact tttggtgctt gtgcatc                                        27

<210> SEQ ID NO 35
<211> LENGTH: 27
<212> TYPE: DNA
<213> ORGANISM: Artificial Sequence
<220> FEATURE:
<223> OTHER INFORMATION: primer

<400> SEQUENCE: 35
aaagtcgaca tggaaaccat taccgtg                                        27

<210> SEQ ID NO 36
<211> LENGTH: 23
<212> TYPE: DNA
<213> ORGANISM: Artificial Sequence
<220> FEATURE:
<223> OTHER INFORMATION: primer

<400> SEQUENCE: 36
aaagtcgacc tcgagggtcg ggc                                            23

<210> SEQ ID NO 37
<211> LENGTH: 32
<212> TYPE: DNA
<213> ORGANISM: Artificial Sequence
<220> FEATURE:
<223> OTHER INFORMATION: primer

<400> SEQUENCE: 37
cctaagctta tggagttttt caaaaagacg gc                                  32

<210> SEQ ID NO 38
<211> LENGTH: 34
<212> TYPE: DNA
<213> ORGANISM: Artificial Sequence
<220> FEATURE:
<223> OTHER INFORMATION: primer

<400> SEQUENCE: 38
actgaattct tagtactgat tgaagatctg ctgg                                34

<210> SEQ ID NO 39
<211> LENGTH: 28
<212> TYPE: DNA
<213> ORGANISM: Artificial Sequence
<220> FEATURE:
<223> OTHER INFORMATION: primer

<400> SEQUENCE: 39
aacaagctta tgtgcttccc gaaggtcc                                      28

<210> SEQ ID NO 40
<211> LENGTH: 34
<212> TYPE: DNA
<213> ORGANISM: Artificial Sequence
<220> FEATURE:
<223> OTHER INFORMATION: primer

<400> SEQUENCE: 40
tttgaattct tattttgagg attggggttc agag                               34

<210> SEQ ID NO 41
<211> LENGTH: 58
<212> TYPE: DNA
<213> ORGANISM: Artificial Sequence
<220> FEATURE:
<223> OTHER INFORMATION: primer

<400> SEQUENCE: 41
gaaacagaat taattgctat agcgtgtact tcgaatctaa tgtgcttccc gaaggtcc     58

<210> SEQ ID NO 42
<211> LENGTH: 58
<212> TYPE: DNA
<213> ORGANISM: Artificial Sequence
<220> FEATURE:
<223> OTHER INFORMATION: primer

<400> SEQUENCE: 42
gaaacagaat taattaatat aacttgtcgt agtcttttaa tgtgcttccc gaaggtcc     58

<210> SEQ ID NO 43
<211> LENGTH: 58
<212> TYPE: DNA
<213> ORGANISM: Artificial Sequence
<220> FEATURE:
<223> OTHER INFORMATION: primer

<400> SEQUENCE: 43
gaaacagaat taattaatgt aaacagtcgt tcgttgagga tgtgcttccc gaaggtcc     58

<210> SEQ ID NO 44
<211> LENGTH: 58
<212> TYPE: DNA
<213> ORGANISM: Artificial Sequence
<220> FEATURE:
<223> OTHER INFORMATION: primer

<400> SEQUENCE: 44
gaaacagaat taattagcat aaattgtttt aggcgtagta tgtgcttccc gaaggtcc     58

<210> SEQ ID NO 45

```
<211> LENGTH: 40
<212> TYPE: DNA
<213> ORGANISM: Artificial Sequence
<220> FEATURE:
<223> OTHER INFORMATION: primer

<400> SEQUENCE: 45
caaaacagcc aagctttatt ttgaggattg gggttcagag                            40

<210> SEQ ID NO 46
<211> LENGTH: 29
<212> TYPE: DNA
<213> ORGANISM: Artificial Sequence
<220> FEATURE:
<223> OTHER INFORMATION: primer

<400> SEQUENCE: 46
ccgggatcct taattttaa agtatgggc                                         29

<210> SEQ ID NO 47
<211> LENGTH: 30
<212> TYPE: DNA
<213> ORGANISM: Artificial Sequence
<220> FEATURE:
<223> OTHER INFORMATION: primer

<400> SEQUENCE: 47
tttgatatct tactacttgt acagctcgtc                                       30

<210> SEQ ID NO 48
<211> LENGTH: 30
<212> TYPE: DNA
<213> ORGANISM: Artificial Sequence
<220> FEATURE:
<223> OTHER INFORMATION: primer

<400> SEQUENCE: 48
tttgatatct tagtactgat tgaagatctg                                       30
```

CORYNEBACTERIUM SP. BACTERIA AND MINICELL DERIVED THEREFROM, AND USE THEREOF

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2015/011154, filed Oct. 21, 2015, which claims priority to the benefit of Korean Patent Application No. 10-2015-0030224 filed in the Korean Intellectual Property Office on Mar. 4, 2015, the entire contents of which are incorporated herein by reference.

TECHNICAL FIELD

The present disclosure relates to *Corynebacterium* sp. bacteria, a *Corynebacterium* sp. bacteria-derived minicell, and a drug delivery system composition including *Corynebacterium* sp. bacteria, a *Corynebacterium* sp. bacteria-derived minicell, or any combinations thereof.

BACKGROUND ART

Conventional cancer treatments using radiation and anti-cancer agents inflict substantial burden on human bodies because they widely harm not only cancer cells but also normal cells. The use of conventional cancer treatments using radiation and anti-cancer agents is limited depending on the age and physical conditions of patients. Also, these treatments may not lead to a complete death of remaining cancer cells due to limitations in therapeutic methods. Recently, technology for delivering a drug in a manner specific to cancer cells by using various drug delivery system, such as liposome, bacteria-derived minicells, micelle, polymer-derived nanoparticles, or bacterial outer membrane vehicles (OMVs), has been introduced (Huang S L, *Adv. Drug Deliv. Rev.* 60:1167-1176(2008), Kim S H, et al., *BBA-Biomembranes* 1788:2150-2159(2009), Savic R, el al., *Science* 300:615-618(2003), Torchilin V P., *Adv. Drug Deliv. Rev.*, 64:302-315(2012), MacDiarmid J A et al., *Cancer Cell*, 11:431-445(2007)). From among these, minicells are bacteria-derived materials and may deliver various drugs (US 2003/0198996 A1), and are receiving much attention due to their high stability and biocompatibility.

Bacterial minicells are a chromosome-depleted cell having a size of about 100 nm to about 400 nm, and do not include chromosome at all. However, RNAs, proteins, cell membrane and wall have the same components or compositions as those of their parent cells. In general, minicell-producing strains can be manufactured by genetically inactivating or over-expressing genes associated with cell division to induce non-equivalent cell division in the course of cell division, and minicell-producing strains are generated from various strains including *Escherichia coli, Salmonella typhimurium, Shigella flexnery, Bacillus subtilis*, or *Listeria monocytogenes* (MacDiarmid J A et al., *Cancer Cell*, 11:431-445(2007)).

When minicells are used for a drug delivery system, lipids and various channel proteins of membrane components can be used in loading or releasing a drug. Also, by changing cell wall or membrane components by using an antibody or an adhesion molecule, cancer-cell targeting and endocytosis into animal cells may be promoted. For example, *Escherichia coli* derived minicells are coated with a bispecific antibody to increase cancer cell directedness, and when loaded with si/shRNA and an anti-cancer agent and treated sequentially, they show high tumor regression effects with respect to cancer cells that are resistant to anti-cancer agents. (MacDiarmid J A et al., *Nat. Biotechnol.*, 27:643-651 (2009)). In this study, however, the minicells derived from *S. typhimurium*, has lipopolysaccharide (LPS) being an endotoxin as a cell wall component, and when this minicell is used as a drug delivery system in vivo, LPS of the minicell may act as a pyrogen, and unexpected immune responses (inflammation), fever, or the like may occur. To address these problems, from among various human strains (normal flora) that have been evolutionarily adapted, a strain that does not have pathogenicity, easy to culture and genetic modification could be selected in order to use as a drug delivery system.

*Corynebacterium glutamicum* is one of normal flora strains existing in vivo and is well adapted to the human immune system, and is one of GRAS (Generally recognized as safe) strains and is highly industrially available due to its use in the production of amino acids and nucleic acids (Nakayama K et al., *Adv. Exp. Med. Biol.*, 105:649-661 (1978)). *Corynebacterium glutamicum* is a gram positive strain, does not have an LPS layer in a cell wall, does not form spores, and compared to other wild-type strains, is easily cultured and genetically modified. Accordingly, when *Corynebacterium glutamicum* is used as a drug delivery system, toxicity problems that may occur from a drug delivery system in itself, for example, LPS of gram-negative bacteria, may be prevented. Moreover, when existing various genetic tools and resources are used, attempt to load drug proteins or target cancer cells may be easily possible.

For genetic modification of *Corynebacterium* sp., a homologous recombination method using sacB screen system (pK19mobsacB) is used to insert genes into a chromosome or delete them therefrom (Schafer A, et al., *Gene*, 145:69-73(1994)). Also, shuttle vectors of *Escherichia coli* and *Corynebacterium* (pCES208, pXMJ19, or the like) can be used to introduce or express foreign genes. For example, human proteins are over-expressed in *Corynebacterium glutamicum* (Date M et al., *Lett. Appl. Microbiol.*, 42:66-70 (2006)). These disclosures may contribute to the production of various eukaryotic cell-derived drug proteins.

Throughout this specification, many papers and patent documents were used as reference in parenthesis. The cited papers and the disclosures of patent documents are in entirety incorporated into the present specification as reference to clearly explain a level of a technical field the present disclosure belongs to and the content of the present disclosure.

SUMMARY

The inventors of the present disclosure made efforts to develop a drug delivery system that safely and effectively delivers a drug and, during drug delivery, hardly shows toxicity to an ambient environment (for example, a nucleic acid, a protein, a cell, a tissue, or the like), in particular, in vivo. As a result, they found that *Corynebacterium* sp. bacteria and *Corynebacterium* sp.-derived minicells effectively deliver a drug in vitro and in vivo and hardly show toxicity, completing the present disclosure.

Objectives and advantages of the present disclosure will be clearly explained by referring to the detailed description, claims, and drawings.

According to an aspect of an exemplary embodiment, a drug delivery system composition includes (1) *Corynebac-* terium sp. bacteria, (2) *Corynebacterium* sp. bacteria-derived minicell, or (3) any combinations thereof.

According to an aspect of another exemplary embodiment, an anti-cancer pharmaceutical composition includes: a drug delivery system composition including a (1) *Corynebacterium* sp. bacteria, (2) *Corynebacterium* sp. bacteria-derived minicell, or (3) any combinations thereof, and a pharmaceutically effective amount of an anti-cancer drug.

A drug delivery system according to embodiments includes *Corynebacterium* sp. bacteria and *Corynebacterium* sp. bacteria-derived minicell. The drug delivery system has high safety for use in vivo compared to other bacteria (for example, *Escherichia coli* (*E. coli*), *Salmonella* sp. bacteria, *Bacillus* sp. bacteria, or the like) or other bacteria-derived drug delivery system.

In various embodiments, when an anti-cancer drug protein expression construct (protein expression recombinant vector or the like) is included, over-expression of anti-cancer drug protein, effectively controlling of protein expression in vivo, and targeting technology using expression of a target factor may be provided.

In various embodiments, a drug is safely delivered in vivo, and accordingly, anti-cancer therapeutic effects may be maximized.

DESCRIPTION OF THE DRAWINGS

FIG. 3 shows the structures of cell surface expression constructs using an auto-transporter protein and sortase-dependent surface expression constructs. affibody and repebody were used as target factor proteins for surface expression.

FIG. 4 shows expression results of target factor protein in *Corynebacterium glutamicum* recombinant strain that has been transformed with a construct manufactured according to Example 5, and the recombinant protein expression was confirmed by Western blot analysis.

FIG. 5 shows ELISA results that confirmed the functionality of targeting factors which is surface expressed in *Corynebacterium glutamicum* recombinant strain. From ELISA results, it is seen that all affibody and repebody on the surface of *Corynebacterium glutamicum* have specificity to HER2 and EGFR.

FIG. 7 shows expression results of drug protein in *Corynebacterium glutamicum*, obtained by using pXMJ19/asparaginase, pXMJ19/IL32β, pXMJ19/IL32γ-transformed recombinant strains.

FIG. 8 shows expression comparison assay results of *Corynebacterium glutamicum* recombinant strain between ramp-tag is applied to IL32β and IL32γ and between ramp-tag is not applied thereto.

FIG. 9 shows whether the functionality of quorum sensing expression system from *Corynebacterium glutamicum* recombinant strains which is transformed with pCES208/luxR-luxI-mCherry and pCES208/luxR-luxI-asparaginase, respectively, and shows the asparaginase expression, which is a drug protein, by applying quorum sensing expression system.

DETAILED DESCRIPTION

Figure 1:
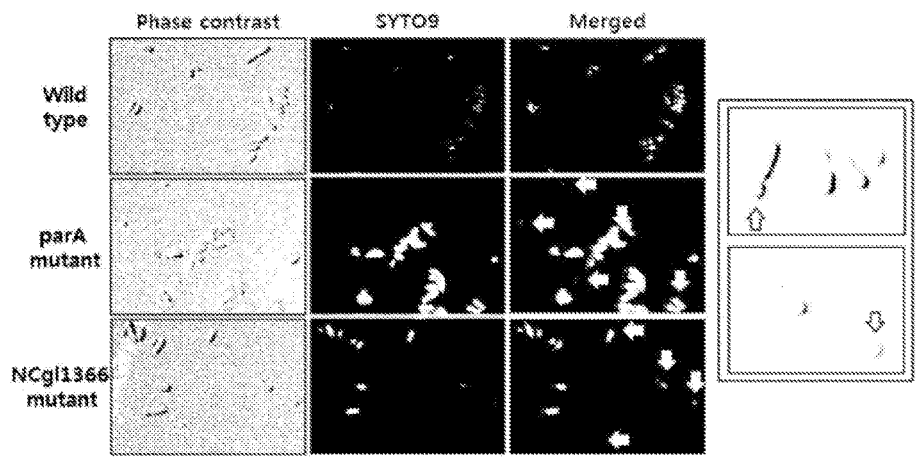
FIG. 1 shows microscopic images of phenotype of wild-type *Corynebacterium glutamicum* and mutant strains (parA, NCgl1366). In the case of mutant strains, longer cells (chromosome included) and small round cells (minicells) were produced together through abnormal dividing. For each of the strain, chromosome DNA was stained by SYTO9. Straining results show that the small round cells in the mutant strain were minicells.

An aspect of the present disclosure provides a drug delivery system composition including (1) *Corynebacterium* sp. bacteria, (2) *Corynebacterium* sp. bacteria-derived minicell, or (3) any combinations thereof.

The inventors of the present application found that *Corynebacterium* sp. bacteria and *Corynebacterium* sp.-derived minicells safely and effectively deliver a drug and, during drug delivery, hardly shows toxicity to the surrounding environment (for example, a nucleic acid, a protein, a cell, a tissue, or the like), in particular, in vivo. Based on this founding, they completed the present disclosure.

In various embodiments, *Corynebacterium* sp. bacteria, which is a drug delivery system, is a gram-positive strain, does not have an LPS layer in its cell wall and does not form spores, and compared with other strains, can be easily cultured and genetically modifiable. Due to these characteristics of *Corynebacterium* sp. bacteria may not show toxicity to the surrounding environment during drug delivery, and may effectively deliver a drug.

In various embodiments, *Corynebacterium* sp. bacteria, as the drug delivery system, may include at least one *Corynebacterium* sp. bacteria selected from *Corynebacterium glutamicum*, *Corynebacterium ammoniagenes*, *Corynebacterium casei*, and *Corynebacterium efficiens*. In various embodiments, *Corynebacterium* sp. bacteria may include at least one *Corynebacterium* sp. bacteria selected from *Corynebacterium glutamicum* and *Corynebacterium casei*. In various embodiments, *Corynebacterium* sp. bacteria may include *Corynebacterium glutamicum*.

The drug delivery system includes: (1) *Corynebacterium* sp. bacteria and (2) a minicell generated therefrom; or (3) *Corynebacterium* sp. bacteria and a minicell generated from *Corynebacterium* sp. bacteria. In various embodiments, the drug delivery system includes *Corynebacterium* sp. bacteria and a minicell generated from *Corynebacterium* sp. bacteria.

A minicell included in the drug delivery system may be a minicell derived from *Corynebacterium* sp. bacteria, and may be manufactured by over-expressing or inactivating several genes involving in cell division of *Corynebacterium* sp. bacteria.

Screening genes associated with cell division of *Corynebacterium* sp. bacteria may be performed by homology searching using Blast P program based on known sequence information about proteins associated with cell division, and these genes may be deleted by tools that are used in the art, for example, SacB screening system (pK19mobsacB).

A method of producing a minicell from *Corynebacterium* sp. bacteria is provided herein as an example only, and genetically structural information about *Corynebacterium* sp. bacteria and why minicells are manufactured are as follows.

Like other gram-positive bacteria, *Corynebacterium* sp. bacteria have DivIVA. However, *Corynebacterium* sp. bacteria are depleted of FtsA, which involves in constriction of wall, and are also depleted of MinC and MinD, which control where ZipA, ZapA, and FtsZ ring, playing an important role in polymerizing FtsZ, are formed (Michel et al., Antonie van Leeuwenhoek 94:99-109(2008)). That is, it is assumed that cell division occurs in a manner different from that of other gram-positive bacteria, and for manufacture of a minicell-producing strain, minicells may be formed by screening out DivIVA, or genes involving in the formation of other walls to manufacture mutants, or changing expression levels.

An aspect of the present disclosure provides a composition including a *Corynebacterium* sp. bacteria-derived minicell.

In various embodiments, a minicell according to embodiments is a minicell that is derived from at least one *Corynebacterium* sp. bacteria selected from *Corynebacterium glutamicum*, *Corynebacterium ammoniagenes*, *Corynebacterium casei*, and *Corynebacterium efficiens*. In various embodiments, a minicell according to embodiments is a minicell that is derived from at least one *Corynebacterium* sp. bacteria selected from *Corynebacterium glutamicum* and *Corynebacterium casei*. In various embodiments, a minicell according to embodiments is a minicell that is derived from *Corynebacterium glutamicum*.

In various embodiments, the drug delivery system is an anti-cancer drug delivery system, and may deliver a drug that has an activity to cancer.

In various embodiments, the cancer may include at least one cancer selected from breast cancer, cervical cancer, ovarian cancer, endometrial cancer, melanoma, bladder cancer, lung cancer, pancreatic cancer, colon cancer, prostate cancer, leukemia, acute lymphoblastic leukemia, chronic lymphocytic leukemia, B-cell lymphoma, acute myelogenous leukemia (AML), chronic myelogenous leukemia, thyroid cancer, thyroid follicular cancer, kidney cancer, spleen cancer, craniocervical disorder, gastric cancer, liver cancer, bone cancer, brain cancer, cholangiocarcinoma, small bowel cancer, uterine cancer and testicular cancer. In various embodiments, the cancer may include at least one cancer selected from breast cancer, cervical cancer, ovarian cancer, endometrial cancer, melanoma, bladder cancer, lung cancer, pancreatic cancer, colon cancer, prostate cancer, leukemia, acute lymphoblastic leukemia, thyroid cancer, kidney cancer, bladder cancer, gastric cancer, liver cancer, brain cancer, small bowel cancer, uterine cancer, and testicular cancer. In various embodiments, the cancer may include at least one cancer selected from breast cancer, cervical cancer and ovarian cancer. In various embodiments, the cancer may include breast cancer.

The drug delivery system has excellent drug delivery function. For example, the drug delivery system may safely and effectively deliver a drug that has anti-cancer activities.

The term 'anti-cancer agent' used herein may be any material that has an anti-cancer activity.

In various embodiments, the term 'drug' used herein refers to an anti-cancer agent, and may include at least one drug selected from a chemical preparation, a protein and a nucleic acid.

In various embodiments, when a chemical preparation is used as the anti-cancer agent, the chemical preparation may include at least one chemical preparation selected from doxorubicin, paclitaxel, docetaxel, cisplatin, carboplatin, oxaliplatin, daunorubicin, epirubicin, idarubicin, valubicin, mitoxantrone, curcumin, gefitinib, erlotinib, irinotecan, topotecan, vinblastine, and vincristine. In various embodiments, the chemical preparation may include at least one chemical preparation selected from doxorubicin, paclitaxel, docetaxel, cisplatin, and carboplatin. In various embodiments, the chemical preparation may include at least one chemical preparation selected from doxorubicin, paclitaxel, and docetaxel.

A method of inserting a drug into *Corynebacterium* sp. bacteria or a minicell derived therefrom may be any method that is known in the art.

When an anti-cancer agent delivered is a protein, the protein may include at least one protein selected from an antibody, a transport protein, a structural protein, a regulatory protein, a hormone, a hormone analogue, a cytokine-derived anti-cancer protein, a cytolysis protein, an amino acid deaminase, an antiangiogenic factor, a cell adhesion molecule, an enzyme inhibitor, a receptor, a fragment of a receptor, and immunotoxin. In various embodiments, the protein may include at least one protein selected from an antibody, a transport protein, a structural protein, a regulatory protein, and a cytokine-derived anti-cancer protein. In various embodiments, the protein may include at least one protein selected from an antibody, an amino acid deaminase, and a cytokine-derived anti-cancer protein. In various embodiments, the protein may include at least one protein selected from an antibody and an amino acid deaminase.

When an amino acid deaminase is included as the anti-cancer agent, the amino acid deaminase may include asparaginase.

When an antibody is delivered as the anti-cancer agent, the antibody includes at least one antibody selected from immunoglobulin, an antibody fragment, and an antibody analogue.

The antibody may include any immunoglobulin that naturally occurs, and may be immunoglobulin G (IgG).

The term 'antibody fragment' used herein includes an antibody fragment having a minimum unit of amino acid sequence that recognizes an antigen, and may include at least one antibody fragment selected from Fab, Fab', F(ab')$_2$, F(ab'), F(ab), Fv, and scFv.

The term 'antibody analogue' used herein refers to an antibody that has a smaller protein molecular weight than an antibody fragment and that recognizes an antigen (for example, an anti-cancer marker factor, an anti-cancer marker protein, or the like) and binds thereto.

When an antibody analogue is included as the antibody, the antibody analogue may exist inside *Corynebacterium* sp. bacteria and a minicell derived therefrom or may be secreted extracellularly, or the antibody analogue may be expressed intracellularly and may bind to a cellular surface and then delivered. The cellular surface binding to *Corynebacterium* sp. bacteria and a minicell derived therefrom may be chemical binding, or may be performed by using an expression vector. For example, through co-expression together with a transport protein, the antibody analogue may move toward and bind to the cellular surface of *Corynebacterium* sp. bacteria and a minicell derived therefrom.

In various embodiments, the antibody analogue may include at least one antibody analogue selected from affibody, repebody, affilin, DARPin, tetranectin, microbody, peptide aptamer, and avimer. In various embodiments, the antibody analogue may include at least one antibody analogue selected from affibody, repebody, affilin, and DARPin. In various embodiments, the antibody analogue may include at least one antibody analogue selected from affibody and repebody.

When the antibody analogue is used, an antibody mimetic may be additionally included.

In various embodiments, examples of the antibody mimetic are affilins (Ebersbach H, et al. *J. Mol. Biol.*, 372:172-185(2007)), affimers (Johnson A, et al. *Anal. Chem.*, 7; 84:6553-6560(2012)), affitins (Krehenbrink M, et al., *J. Mol.* 383:1058-1068(2008)), anticalins (Skerra A, et al., *FEBS J.*, 275:2677-2683(2008)), avimers (Silverman J, et al., *Nat. Biotechnol.*, 23:1556-1561(2005)), and monobodies (Koide A, et al., *Methods Mol. Biol.*, 352:95-109 (2007)). The antibody mimetic may be manufactured in such a way that the antibody mimetic targets a particular receptor or antigen, and a manufacturing method thereof available herein may a panning method. An antibody mimetic target factor has a smaller molecular mass than an antibody and a simple structure. Accordingly, the antibody mimetic target factor is relatively easily expressed in bacteria, and is manufactured in the form of a fusion protein, leading to ease of application.

When a drug for the drug delivery system includes a nucleic acid as an anti-cancer agent, the nucleic acid may be any nucleic acid that suppresses the expression of an cancer-specific (causing) gene. The suppressing may include, for example, binding to a nucleic acid that expresses a cancer-causing gene or binding directly to the cancer-causing gene.

The nucleic acid may exist in or outside *Corynebacterium* sp. bacteria and a minicell, or may exist being operatively linked to a construct expressing a nucleic acid.

In various embodiments, the nucleic acid as a delivery drug may include at least one nucleic acid selected from siRNA, shRNA, miRNA, antisense RNA, LincRNA, ribozyme, and peptide nucleic acids (PNA), In various embodiments, the nucleic acid may include at least one nucleic acid selected from siRNA, shRNA, miRNA, and antisense RNA. In various embodiments, the nucleic acid may include at least one nucleic acid selected from siRNA and shRNA.

In various embodiments, the drug delivery system composition may include a construct that expresses a protein. The construct may express a drug protein directly in the drug delivery system or in a drug receptor (for example, a cancer cell or a cancer tissue).

The term 'construct' used herein refers to a gene expression structure that expresses a protein in prokaryote or a eukaryote. In particular, the term 'construct' includes a construct that expresses a protein in a mammal cell from a drug-delivered bacterium or minicell.

For example, the construct may include a construct that includes *Corynebacterium* sp. bacteria or a minicell derived therefrom which is introduced into an animal cell by receptor-mediated endocytosis to express a protein in an animal cell, and a construct that includes a protein expression system by a quorum sensing system, a protein is expressed in *Corynebacterium* sp. bacteria or a minicell derived therefrom and secreted extracellularly.

The term 'quorum sensing' used herein refers to a system in which when a cell population density reaches a particular level, cells transmit signals one another via chemical language (metabolic product) produced by themselves, and through which expression of a particular gene is controlled. This system has an individual density-dependent quorum sensing gene expression logic, and is performed by a protein that synthesizes a signal material and a transcription regulatory protein that is to bind to the signal material to control expression of a gene.

In various embodiments, when quorum sensing is used, the protein expression construct may include a gene circuit consisting of LuxI gene, LuxR gene, and LuxI promoter.

In various embodiments, when a drug protein is expressed as, in particular, an anti-cancer agent or targeting ligand, the protein expression construct may include a construct that expresses at least one drug protein selected from an antibody, an antibody derivative, an antibody mimetic, and a cell adhesion molecule.

In various embodiments, the drug delivery system composition includes a protein expression construct. In various embodiments, the protein expression construct may include a polynucleotide sequence that encodes (1) an anti-cancer protein, (2) an anti-cancer protein and a cancer cell surface receptor-binding protein, or (3) an anti-cancer protein and a cancer cell surface antigen-binding protein.

The drug delivery system composition may include a construct that expresses a protein (for example, an antibody, an antibody analogue, a receptor, a cell surface antigen-binding protein, or the like) that may bind to an anti-cancer target factor to effectively deliver a drug having an anti-cancer activity to a cancer cell or tissue, and the protein that is to bind to an anti-cancer target factor may be positioned on an external membrane surface of *Corynebacterium* sp. bacteria and a minicell derived therefrom.

The term 'cancer cell surface receptor-binding protein' used herein refers to a receptor-binding protein that is to bind to a cancer cell surface, and the term 'cancer cell surface antigen-binding protein' used herein refers to a polypeptide or protein that may bind to a cancer cell surface antigen.

In various embodiments, the construct may include internalin A as the cancer cell surface antigen-binding protein that is to bind to an anti-cancer target factor. Accordingly, after binding to the animal cell surface, a drug may be delivered into an animal cell by endocytosis. For example, internalin A is expressed on the surface of *Corynebacterium* sp. bacteria or *Corynebacterium* sp. bacteria-derived minicell and then, binds to cancer cell surface E-cadherin, thereby being introduced into a cancer cell. When the cancer cell surface antigen is included, the cancer cell surface antigen-binding protein may include internalin A.

To anchor a protein in bacterial surface, cancer cell receptor or cell surface antigen-binding protein which is to bind to an anti-cancer target factor, sortase may be expressed in order to anchor to the surface of *Corynebacterium* sp. bacteria and a *Corynebacterium* sp. bacteria-derived minicell. To do this, together with the protein, cancer cell receptor- or cell surface antigen-binding protein which is to bind to an anti-cancer target factor, a nucleotide sequence that encodes asparaginase may be additionally included in a construct as an anticancer drug protein.

In various embodiments, the drug delivery system composition includes a protein expression construct that includes (1) an anti-cancer protein and a cancer cell surface receptor-binding protein and (2) a polynucleotide sequence that encoding anti-cancer protein or a cancer cell surface receptor-binding protein. In various embodiments, the drug delivery system composition includes a protein expression construct that includes a polynucleotide sequence that an anti-cancer protein or a cancer cell surface receptor-binding protein.

When the anti-cancer protein, the cancer cell surface receptor-binding protein, or the cancer cell surface antigen-binding protein is used, a drug may be delivered even into solid cancer tissues, to which an anti-cancer drug is difficult to reach, as well as conventional cancer cells.

In various embodiments, when a drug or receptor-binding protein is expressed as the drug, a flexible linker may be included in the protein expression construct to maintain the structure of the drug or receptor-binding protein and to strengthen flexibility on the surface of Corynebacterium sp. bacteria or Corynebacterium sp. bacteria-derived minicell.

The protein linker used herein includes any protein linker that is known in the art, and a polynucleotide sequence of a known protein linker may be constituted based on a codon sequence.

The protein linker used herein includes a linker that connects one protein and another protein, and a linker that connects a protein and a substrate that chemically binds thereto. The term 'chemically binding' used herein is considered as having the same meaning as a chemical bond, and may include a covalent bond, an ion bond, a hydrogen bond, or the like.

In various embodiments, the protein expression construct may include a polynucleotide sequence that encodes a protein linker.

When the drug delivery system composition includes a drug protein expression construct, the drug protein expression construct may include a polynucleotide that encodes a ramp tag to increase expression of drug protein.

The term 'ramp tag' used herein refers to a tag that is attached to recruit rare tRNA in advance before a gene to prevent a decrease in expression efficiency due to translation delay effects caused by rare codon during translation of the gene. Unlike in the case of codon optimization, an original ORF sequence is not changed and accordingly, DNA artificial synthesis due to codon substitution is not needed, leading to low costs. The ramp tag is designed according to a particular logic by referring to a rare codon list for a host, and a theory and method related thereto are described in KR 10-2014-0112888, and this patent document is incorporated into this specification by reference.

Another aspect of embodiments provides an anti-cancer pharmaceutical composition including the drug delivery system and a pharmaceutically effective amount of an anti-cancer drug as an active ingredient.

The anti-cancer pharmaceutical composition includes, as a carrier to effectively deliver an anti-cancer drug to cancer cells or cancer tissues, the drug delivery system including Corynebacterium sp. bacteria, Corynebacterium sp. bacteria-derived minicell.

The anti-cancer pharmaceutical composition shows excellent anti-cancer effects in vitro as well as in vivo.

The anti-cancer effects are embodied by synergy effects simultaneously including recognition of cancer cells and cancer tissues and drug delivery, obtained by allowing an anti-cancer drug to be present inside a cell and on the surface thereof via a drug delivery system including Corynebacterium sp. bacteria and a minicell derived therefrom.

The term "pharmaceutically effective amount" used herein refers to a sufficient amount to obtain efficacy or activities (that is, cancer cell growth inhibition or cancer cell death) of the anti-cancer drug. The anti-cancer pharmaceutical composition may additionally include a pharmaceutically acceptable carrier.

The pharmaceutically acceptable carrier included in the pharmaceutical composition may be any carrier that is conventionally used in preparing medications, and may be selected from lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, and mineral oil, but is not limited thereto.

The anti-cancer pharmaceutical composition may be administered in an appropriate amount, which varies depending on various factors including a preparation method, an administering method, the age, body weight, gender, or morbidity of a patient, food, an administering time, an administering path, an excretion rate, and response sensitivity. The anti-cancer pharmaceutical composition may be orally or non-orally administered. When the anti-cancer pharmaceutical composition is non-orally administered, the non-oral administration may be performed by bolus injection, intravenous injection, subcutaneous injection, intramuscular injection, intraperitoneal injection, transdermal administration, or the like. In various embodiments, the anti-cancer pharmaceutical composition may be administered by injecting directly into blood vessels (for example, bolus injection or intravenous injection). The injecting directly into blood vessels means administering into blood vessels including arteries, veins, and capillaries, for example, aorta, carotid, subclavian arteries, celiac arteries, mesenteric arteries, renal arteries, iliac arteries, arterioles, capillaries, and veinlets. The administration method may be appropriately changed depend on where a blood vessel having blood clots is located.

The administering path for the anti-cancer pharmaceutical composition may vary depending on the kind of disease and a determination of a physician. For example, a concentration of an active ingredient included in the anti-cancer pharmaceutical composition may vary depending on a therapeutic purpose, the physical state of a patient, or how long the active ingredient is needed. The concentration of an active ingredient is not limited to a particular concentration. In various embodiments, a daily dose of the pharmaceutical composition may be in a range of 0.001 to 1,000 mg/kg.

The anti-cancer pharmaceutical composition may be formulated by using a pharmaceutically acceptable carrier and/or an excipient according to a method that is easily performed by one of ordinary skill in the art. The anti-cancer pharmaceutical composition may be formulated in a unit dose or loaded into a multi-dose container. In this regard, the formulation may be in the form of solution, suspension, or emulsion in oil or aqueous medium, or in the form of extract, powder, granule, tablet, or capsule. In various embodiments, the formulation may further include a dispersant or a stabilizer.

Hereinafter, embodiments will be described by referring to Examples. However, these examples are provided herein only for illustrative purpose only, and do not limit the scope of the inventive concept. These are understood by one of ordinary skill in the art.

EXAMPLE 1

Bacteria Strain, Medium and Culture Conditions

In experiments used herein, *Escherichia coli* (*E. coli*) XL1-Blue [endA1 gyrA96 (nalR) thi-1 recA1 relA1 lacglnV44 F'[::Tn10 proAB+lacIΔ(lacZ)M15] hsdR17(rK-mK+)], JM110 [rpsL thr leu thi lacY galK galT ara tonA tsx dam dcm glnV44 Δ(lac-proAB) e14– [F' traD36 proAB+ lacIq lacZΔM15] hsdR17(rK-mK+)] was used as a host cell for gene cloning, and *Corynebacterium glutamicum* (*C. glutamicum*) ATCC13032 (American Type Culture Collection) was used as a host cell for manufacturing a drug delivery system. *E. coli* and *C. glutamicum* strain used herein were cultured by using Luria-Bertani (LB) media (available from Difco Company) at temperatures of 37° C. and 32° C., respectively, and during the culturing, an appropriate amount of antibiotics (Kanamycin 20 μg/ml, Chloramphenicol 10 μg/ml, Ampicillin 50 μg/ml) was added thereto, if needed.

EXAMPLE 2

Manufacture and Transformation of Competent Cells

*E. coli* (*E. coli* XL1-Blue, JM110) competent cells were manufactured as follows. First, cells were cultured on LB plate media, and then, a single colony was inoculated to liquid media and pre-cultured. Then, the cells were subcultured in 20 ml of MgCl$_2$-supplemented SOB media, and cultured at a temperature of 22° C. When the value of OD 600 nm was 0.5, the cells were recovered and treated with a Inoue transformation buffer. The resultant cells were stored at a temperature of –80° C. before use. Transforming was performed according to a conventional heat shock method in which every recombinant DNA was mixed with competent cells and then placed in ice for 30 minutes, and then, heat-shocked at a temperature of 42° C. for 90 seconds, and left in ice for 2 minutes. Thereafter, after culturing at a temperature of 37° C., the cells were spread on an LB solid media including appropriate antibiotics to induce growth for about 15 to 20 hours, and then, clones with a target gene inserted thereinto were obtained by colony cracking and colony PCR.

*Corynebacterium glutamicum* (*C. glutamicum*) competent cells were produced as follows. Cells were cultured on LB plate media, and then, a single colony was inoculated in a 2% glucose-containing LB liquid media and pre-cultured, and the resultant culture was inoculated in an amount of 1 to 2% into LB media (called Epo medium) containing isonicotinic acid hydrazide (isoniazid; 4 μg/ml), glycine (25 μg/ml), and Tween 80(0.1%)), and then cultured at a temperature of 25° C., and when the value of OD 600 nm was 0.6, the cells were recovered, followed by washing four times with 10% glycerol, thereby completing the preparation of electrocompetent cells. These cells were divided into aliquots of the suspensions into chilled, sterile microfuge tubes, each containing 100 μl of cells, and stored at a temperature of –80° C. before use. To increase transformation yield of *Corynebacterium glutamicum*, the vectors used for *Corynebacterium glutamicum* was initially transformed with JM110, and then, methylation pattern-free recombinant vectors were recovered. *Corynebacterium glutamicum* was transformed by electroporation as follows: 200 to 500 ng/μl of recombinant plasmid was added to 100 μl of electrocompetent cells, and then, a current was applied by using an electroporating device (Bio-Rad, USA) in conditions including 0.2 cm cuvette, 25 uF, 600 ohm, 2.5 kV, and 10-12 ms, immediately followed by heat shock at a temperature of 46° C. for 6 minutes (van der Rest M E, et al., Appl. *Microbiol. Biotechnol.*, 52:541-545(1999)). Thereafter, 1 ml of SOC medium was added thereto, and the cells were cultured at a temperature of 32° C. for 1.5 hours. The resultant was smeared on a LB solid media including appropriate antibiotics to select recombinant strains.

EXAMPLE 3

Production of Minicell-Producing Strain from *Corynebacterium* and Separation of Minicell Therefrom A minicell-producing strain was developed from *Corynebacterium glutamicum* (*C. glutamicum*) by inactivating genes which is related to cell division.

The searching for such a gene was confirmed by Blast P search based on an amino acid sequence of minCDE of *E. coli*. As a result, it was confirmed that MinD of *E. coli* has, respectively, identities of 22%, 24%, and 18% of parA, NCgl1366, and mrp of *Corynebacterium*. Even with low identities to minD, these proteins all were confirmed to be a protein associated with cell division (description; putative cell division protein, chromosome partitioning ATPase), and accordingly, an experiment for manufacturing deletion mutant strains for these genes (parA, NCgl1366, mrp) was performed.

The deleting a gene from *Corynebacterium glutamicum* was performed by inducing homologous recombination using a pK19mobsacB vector and selecting a mutant strain. To manufacture homologous arms, top and bottom fragments of each of the genes were amplified by PCR using primers shown in Table 1 until the length was about 500 bp. These two homologous arms were connected to a template by overlapping PCR, and then, cloned to a pK19mobsacB vector. Thereafter, *Corynebacterium glutamicum* was transformed therewith, and then, selecting was twice performed by using antibiotics and 10% sucrose to search for a gene-deleted mutant. Finally, colony PCR was performed by using a check primer to obtain a target gene-deleted mutant strain. As a result, a mutant strain deleted of parA gene and a mutant strain deleted of NCgl1366 gene were obtained, respectively. In the case of mrp, although this experiment was performed three or more times, a mutant strain depleted of mrp was not obtained. This may be due to the fact that in the case of Mrp, since Mrp is a necessary protein for essential physiology of *Corynebacterium glutamicum*, it is considered that a mutant strain is not generated. Table 1 shows primer polynucleotide sequences used in order to manufacture the mutant strains.

TABLE 1

| name | sequence (5' →3') | restriction enzyme | SEQ ID NO: |
|---|---|---|---|
| ParA P1 | ATAAGCTTCGGCTGCATGAGGCC | HindIII | 1 |
| ParA P2 | CGTCGCAGTAAACTTCTTTGAATACGTTAATTG | – | 2 |

TABLE 1-continued

| name | sequence (5' →3') | restriction enzyme | SEQ ID NO: |
|---|---|---|---|
| ParA P3 | TACTGOGACGTCAACCATCOCTATC | — | 3 |
| ParA P4 | ATAGGATOCACGCCCAGATCTCAACATC | BamHI | 4 |
| ParA C1 | CAATCGCCGGGATAACC | — | 5 |
| ParA C2 | ATTCTAAACTGTGGTGTCATCGG | — | 6 |
| 1366 P1 | ATGGATCCATTGAGCTTCGTAATTAACGGG | BamHI | 7 |
| 1366 P2 | ACAACATTTAACAAATTTCGGCGCG | — | 8 |
| 1366 P3 | TAAATGTTGTTTTTCTAAAAACCACGCC | — | 9 |
| 1366 P4 | ATAAGCTTCAATTOGAGATCATCTTCATCG | HindIII | 10 |
| 1366 C1 | CAGATGGCGGGAATTCTCG | — | 11 |
| 1366 C2 | AGACAGCGCGCGGG | — | 12 |
| arp P1 | ATAAGCTTTATTTACATTTTCTGAAAGACCGG | HindIII | 13 |
| arp P2 | GATACTATCGGTCCAAGAGACGCC | — | 14 |
| arp P3 | CGATAGTATCGATAGTAGTCCCAAGTTTTGATAC | — | 15 |
| arp P4 R | ATCCCGGGGAAAAAGTAGCCCGGTTCTTTG | AvaI | 16 |
| arp C1 | CAGAGAATTTAGCAATGCAGCG | — | 17 |
| arp C2 | CACCCATGGCTGATTTCAA | — | 18 |

Under microscope, it was confirmed that, unlike normal strains, these two mutant strains (parA, NCgl1366) showed unequal division during cell division. The microscopic image had a long cell and a small spherical cell, which was like a minicell. Whether the minicell-like cell is a minicell, chromosomal DNA was stained by using SYTO9 and observed under a fluorescence microscope (OLYMPUS BX43 U-RFL-T). As a result, it was confirmed that the small spherical cell contains little fluorescence or does not contain fluorescence at all.

This result shows that the produced small spherical cell was a minicell (FIG. 1). Also, in the case of NCgl1366 mutant strain, together with the minicell, an anucleate cell was also identified. This result shows that these two mutant strains all can be used as a minicell producing strain. As other methods for producing a minicell producing strain, a minicell producing strain can be manufacture by deleting other genes associated with cell division or by inducing perturbation during cell division through over-expression of a protein associated with cell division.

The separating a minicell from a parA mutant strain was performed by centrifuging, and treating with antibiotics. A mutant strain was inoculated to 200 ml of LB liquid media and then cultured at a temperature of 30° C. When the value of OD 600 nm was 2.0, centrifuging was performed at a gravity of 2,000 g for 10 minutes to remove parental cells. Then, a supernatant was centrifuged at a gravity of 10,000 g for 10 minutes and then recovered. Then, recovered minicell pellets were resuspended in 50 ml LB media, and cultured at a temperature of 30° C. for 20 minutes, and then, antibiotics (streptomycin 50 ug/ml) were added thereto, and culturing was performed thereon for 1 hour to kill the remaining parental cells. Thereafter, centrifuging was performed thereon at a gravity of 400 g for 5 minutes to remove cell debris therefrom, and then, the supernatant was centrifuged at a gravity of 10,000 g for 10 minutes and the minicell was recovered. The resultant minicell was subjected to viable cell counting to confirm a contamination level of parental cells. As a result, it was confirmed that less than 100 cfu/ml of parental cells were contaminated. The number of finally separated minicells was about $3 \times 10^{10}$ cells at an initial culturing of 200 ml of cells.

EXAMPLE 4

Figure 2:
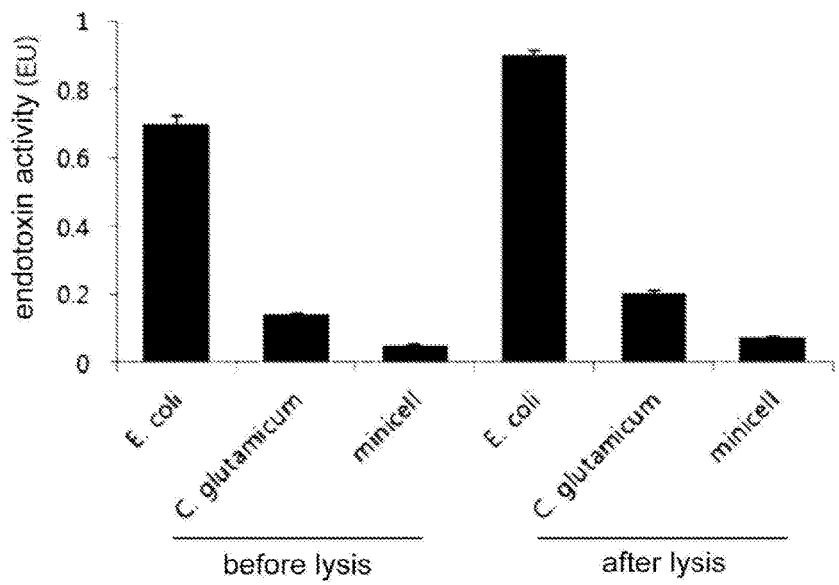
FIG. 2 shows LAL (*Limulus amebocye* lysate) assay results on endotoxin activity in *Corynebacterium glutamicum* and *Escherichia coli*. The results show that compared to *Escherichia coli*, *Corynebacterium glutamicum* hardly shows endotoxin activity.

Evaluation on Endotoxin Activity of Corynebacterium-Derived Drug Delivery System Corynebacterium glutamicum, a gram positive strain, does not have lipopolysaccharide (LPS) which mainly causes endotoxin activity in its cell wall. However, Corynebacterium glutamicum has a thin peptidoglycan layer and arabinogalactan binding thereto, and in addition, has a mycolic acid layer acting as an outer membrane of Gram-negative bacteria, and free polysaccharides, glycolipids, and a protein (S-layer protein, pili, or the like) on the surface of a cell wall (A Burkovski et al., *ISRN Microbiol.* 2013:11 (2013)). Up until now, it is not known whether these constituting materials cause endotoxicity. Herein, whether these constituting materials cause endotoxicity was confirmed by using LAL chromogenic endotoxin quantification kit (available from Thermo scientific Company) while *E. coli* is used as a control. For this experiment, a minicell separated from wild-type *Corynebacterium glutamicum* (*C. glutamicum*) and a minicell separated from parA mutant strain were used, and these minicells were compared before and after sonication for lysis. As a result, *Corynebacterium glutamicum* and minicell showed substantial low levels of endotoxin activity compared to *E. coli* (FIG. 2).

EXAMPLE 5

Manufacture of Recombinant Vector for Surface Expression of Cancer Cell Targeting (Receptor or Antigen-Binding Protein) Factors Herein, affibody (bind to HER2) and repebody (bind to EGFR) were used as cancer cell targeting factors. Surface expression of affibody and repebody on *Corynebacterium glutamicum* was embodied by using a method in which (1) a membrane protein is used as an auto-transporter to produce a fusion protein, and a method in which (2) a targeting factor protein is anchored in a sortase-dependent manner on a cell wall peptidoglycan layer, respectively. First, a targeting protein was surface-expressed on *Corynebacterium glutamicum* by using auto-transporter, and an example of such a protein was α-amylase (W Yao et al., *Arch. Microbiol.*, 191:751-759(2009)), and this experiment was performed by referring to this disclosure.

To do this, primers shown in Table 2 were used and an affibody gene and a repebody gene, which are target proteins for surface expression, were amplified. NCgl1221 gene, which was to be used as an auto-transporter, was amplified by PCR, using genomic DNA of *Corynebacterium glutamicum* as a template. In this regard, to obtain the function of NCgl1221 auto-transporter, 423 amino acids of N-terminus including a signal sequence were allowed to be translated, a linker sequence (SSSSGSSSSG) and a tag sequence (Myc-tag, His-tag) were designed to be included, and affibody and repebody were located on C-terminus to be express as a fusion protein. NCgl1221 gene were cleaved by Hind III and KpnI, affibody and repebody, each including a linker sequence and tag sequence, were cleaved by KpnI and SacI and then cloned in pXMJ19 vector, and finally, a pXMJ19 recombinant vector including an NCgl1221-affibody construct and an NCgl1221-repebody construct was manufactured (FIG. 3A). Table 2 shows primer polynucleotide sequences for manufacturing surface expression proteins using auto-transporters.

TABLE 2

| name | sequence (5' →3') | restriction enzyme | SEQ ID NO: |
|---|---|---|---|
| 1221-423F | AAAAAGCCTATGATTTTAGGCGTACCC | HindIII | 19 |
| 1221-423R | AAAGGTAOCTCCACAGTCATGACCTTAA | KpnI | 20 |
| affi-F | TTTGGTACCTCTTCCTCATCGGG | KpnI | 21 |
| affi-R | TCGGAGCTCTCATTTTGGTCGTTG | SacI | 22 |
| repe-F | TTAGGTACCATGGAAACCATTACCGTG | KpnI | 23 |
| repe-R | AAAGAGCTCGCTTTGTTAGCAGCCG | SacI | 24 |

For sortase-dependent surface expression, *Listeria monocytogene* (KCTC13064)-derived sortase (srtA) and a signal sequence and a structure sequence of internalin A (inlA), which is known as a sortase-dependent surface expression protein, were used to design a fusion protein (WD Schubert et al., Cell 111:825-836(2002)). To obtain a gene source, *Listeria* bacteria was obtained and cultured on Brain Heart Infusion solid media, and genomic DNA was extracted from the cultured strain. While the genomic DNA was used as a template, sortase and internalin gene were amplified by using primers shown in Table 3. Table 3 shows primer polynucleotide sequences used to manufacture sortase-dependent surface expression proteins.

TABLE 3

| name | sequence (5' → 3') | restriction enzyme | SEQ ID NO: |
|---|---|---|---|
| srtA F | TTAGATATCGGGAAAACTCTTTTTGATAGTAAC | EcoRV | 25 |
| srtA R | CCAGATATCGGATGGTAATGAGAAATTATTGC | EcoRV | 26 |
| inlA F | TAAGGATCCATGAGAAAAAAACGATATGTATGG | BamHI | 27 |
| inlA R | TTACTGCAGCTATTTACTAGCACGTGCTTT | PstI | 28 |
| inlA_h R | TGATGGTGATGGTGATGCATTTTTGAATTATAAGGGTCATAAGC | — | 29 |
| inlA_h F | ATGCATCACCATCACCATCACGAAGCTTCACTCCCTACA | — | 30 |
| inlass R | AAAGTCGACAACTTGGTCTAGATCTGTTTG | SalI | 31 |

TABLE 3-continued

| name | sequence (5' → 3') | restriction enzyme | SEQ ID NO: |
|---|---|---|---|
| Flg F | AAAGTCGACCCCGTAAAAGAAGGTCAC | SalI | 32 |
| affi-S F | AAAGTCGACAACAAATTCAACAAAGAAATGAG | SalI | 33 |
| affi-S R | AAAGTCGACTTTTGGTGCTTGTGCATC | SalI | 34 |
| repe-S F | AAAGTCGACATGGAAACCATTACCGTG | SalI | 35 |
| repe-S R | AAAGTCGACCTCGAGGGTCGGGC | SalI | 36 | pCXS35 and pCXI40 vectors with *Corynebacterium*-derived constitutive expression promoters (Psod, PilvC) were used (J Lee et al, *J. Microbiol. Biotechnol.*, 24:70-79 (2014)). Sortase gene including a promoter and terminator sequence of a wild-type strain was cloned in KpnI site, and internalin A was treated with BamHI and PstI restriction enzymes and then cloned. That is, pCXS35 and pCXI40 recombinant vectors including srtA, inlA, and srtA-inlA constructs were manufactured. Thereafter, a portion of internalin A that is to bind to E-Cadherin was replaced with affibody and repebody for expression of a fusion protein, and primers shown in Table 3 were used as a recombinant vector. The designed gene included the signal sequence and Cap sequence of N-terminus of internalin A, the structure sequence and sortase-dependent sequence of C-terminus of internalin A, and affibody gene and repebody gene inserted between the Cap sequence and the structure sequence. Ultimately, pCXS35/srtA and pCXI40/srtA recombinant vectors including inlAss-affibody construct and inlAss-repebody construct were manufactured. For Western blot analysis, a construct in which histidine tag ($H_6$) was located before LPXTG motif, which is a sortase recognition site, was manufactured (FIG. 3B).

EXAMPLE 6

Confirmation of Surface Expression of Cancer Cell Target Factor on *Corynebacterium*

NCgl1221-affibody, NCgl1221-repebody, srtA, inlA, srtA-inlA, inlAss-affibody, inlAss-repebody constructs, as used or manufactured in Example 5, were used to transform *Corynebacterium* in the same manner as described in Example 2 to manufacture recombinant strains. In the case of NCgl1221-affibody and NCgl1221-repebody, which are surface expression constructs manufactured using an auto-transporter, recombinant strain single colonies cultured on Chloramphenicol (10 μg/ml)-supplemented LB solid media were pre-cultured in a 15 ml test tube, and then, 1% thereof was inoculated to 100 ml flask and cultured at a temperature of 32° C. at a rotation rate of 200 rpm. Thereafter, when the value of OD 600 nm was 0.5, 1 mM IPTG (Isopropyl β-D-1-thiogalactopyranoside) was added thereto to induce protein expression, and cultured for 3 to 6 hours. The cells were recovered at certain time intervals. InlAss-affibody and inlAss-repebody, which are sortase-dependent surface expression constructs, were cultured in Kanamycin (20 μg/ml)-supplemented media. In the case of pCX series vector, since pCX series vector is a constitutive expression vector, a sample was recovered at certain time intervals after being cultured without a separate inducing material. Expression of the recombinant proteins was confirmed by SDS-PAGE and Western blot analysis. As a result, in the case of a surface expression construct manufactured by using an auto-transporter, NCgl1221-affibody was expressed well and thus an expression band was distinctive on Western blot analysis, but the expression band of NCgl1221-repebody was not confirmed. This may be due to the fact that since repebody is greater than affibody in size, surface expression of repebody may be relatively difficult to be performed. Secondly, inlAss-affibody and inlAss-repebody, which are sortase-dependent surface expression constructs, were confirmed by SDS-PAGE and Western blot analysis. As a result, it is seen that these two fusion proteins were all expressed on *Corynebacterium* (FIG. 4).

EXAMPLE 7

Confirmation on Specificity of *Corynebacterium* Drug Delivery System with Respect to HER2, EGFR Over-Expression Cancer Cells To confirm specificity of affibody and repebody with respect to HER2 and EGFR, electrocompetent cells were manufactured by using minicell-generating *Corynebacterium glutamicum* strain (*C. glutamicum* parA) in the same manner as in Example 2, and then, used to manufacture a recombinant strain transformed with pCXI40/inlAss-affibody or pCXI40/inlAss-repebody.

Thereafter, minicells with surface-expressing target factors of affibody and repebody were harvested in the same manner as in Example 3. The specificity of affibody and repebody with respect to HER2 and EGFR was confirmed by performing enzyme linked immunosorbent assay (ELISA). For example, HER2 or EGFR was added in a 96-well plate, and left in itself overnight at a temperature of 4° C., and then, reacted by using a blocking buffer (2% skim milk in PBS) for two hours at a temperature of 25° C., and washed three times by using a wash buffer (0.1% Tween-20), and thereafter, the affibody and repebody-surface expressing minicells were added thereto and reacted at a temperature of 25° C. for 2 hours. In this regard, minicells that do not express anything were used as a control. Then, the plate was washed three times with a wash buffer, and a primary antibody (α-affibody, α-repebody, and Abcam) was added thereto and reacted for about 1 hour, and then, the resultant was washed three times with a wash buffer. Then, HRP (horseradish peroxidase)-binding secondary antibody was added thereto and reacted for about 1 hour, and the resultant was washed. After reaction with HRP substrate (tetramethylbenzidine: BD OptEIA), an absorbance was measured by using a laser scanner (infinite M200: TECAN) at a wavelength of 450 nm.

Experimental results show that the minicells that surface-expressed affibody or repebody showed specificity with respect to HER2 and EGFR, and the nothing-expressing minicells did not show the specificity (FIG. 5).

To confirm specificity with respect to cancer cells, *Corynebacterium glutamicum* minicells manufactured in the same manner as described above were reacted with a breast cancer cell to compare cell uptake levels. Human breast cancer cell lines having a certain expression level of HER2 or EGFR were selected as an experimental group, and cultured (K Subik et al., Breast Cancer, 4:35-41(2010)). SKBR-3(HER2:+, EGFR:+), MDA-MB-453(HER2:−, EGFR:−), MDA-MB-435 (HER2:+, EGFR:−) breast cancer cell lines were cultured at a temperature of 37° C., in a 5% carbon dioxide condition, in 10% FBS (Fetal Bovine Serum; Gibco, Invitrogene) and 1% antibiotics (Penicillin, streptomycin, Gibco, Invitrogene)-supplemented DMEM (Dulbecco's modified Eagle medium; Hyclone, Thermal scientific) or RPMI (Roswell Park Memorial Institute medium; Hyclone, Thermal scientific) media. For example, SKBR-3, MDA-MB-453, MDA-MB-435 breast cancer cell lines were cultured, gelatin-coated coverslips were placed on a 12 well culture plate, and about $1\times10^7$ breast cancer cells were placed thereon per each well and cultured. After about 12-16 hours of cultivation, when a confluence was about 70%, the cell lines were co-incubated with minicells. For this reaction with minicells, the media was replaced with OPTIMEM media, and minicells were added thereto, and reacted for about 4 hours at a temperature of 37° C. Then, the resultant was washed three times with PBS to remove the remaining minicells. After the washing, 4% (w/v) PFA (paraformaldehyde) was added thereto and reacted for 10 minutes to fix cells. The cells were washed, and then, treated with 0.1% Triton x-100 for 10 minutes. Thereafter, the resultant was reacted with 1% BSA for 1 hour at room temperature, and then, staining was performed thereon by using phallotoxin for 20 minutes. Then, the resultant was washed with PBS, and a coverslip was mounted by using a mountant (prolong Gold reagent DAPI), and then, identified by fluorescence microscope (OLYMPUS BX43 U-RFL-T) at a magnification ratio of 1,000.

Figure 6:
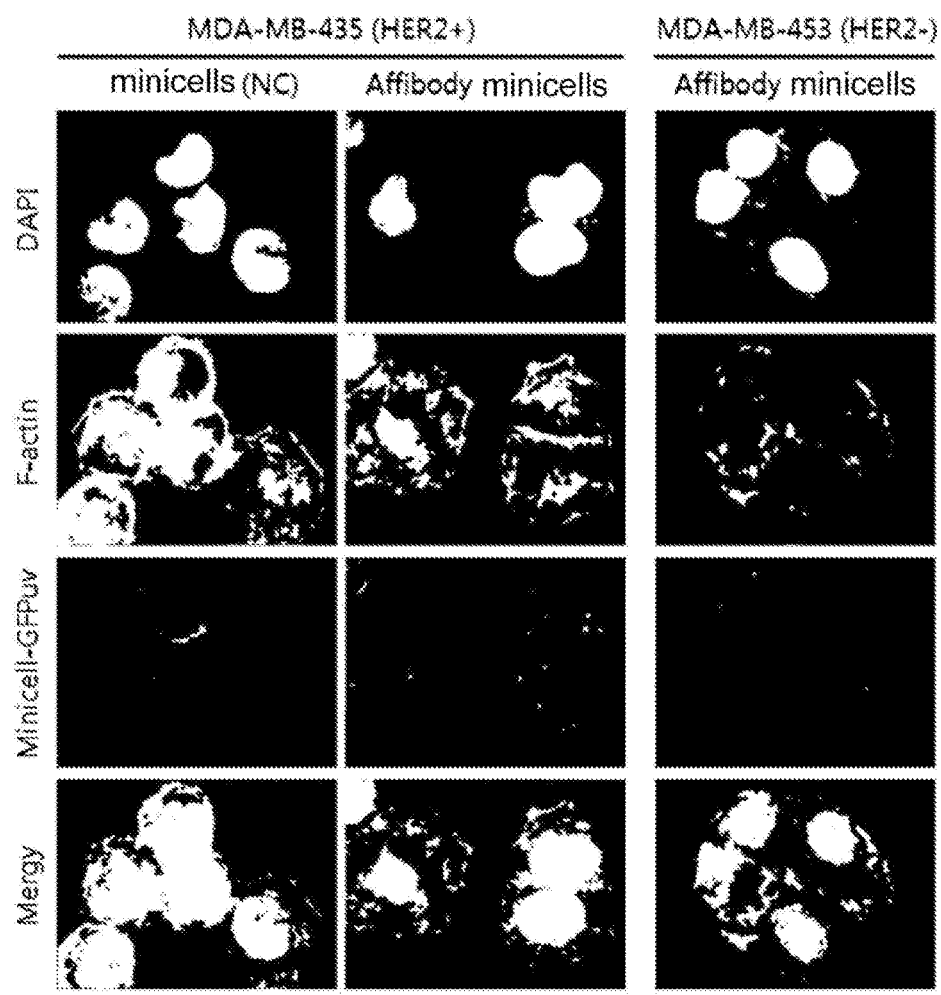
FIG. 6 shows immunofluorescence staining images of breast cancer cell, used to compare cell uptake activities. To identify cell uptake levels, breast cancer cell MDA-MB-435 (HER2+) and MDA-MB-453(HER2−) were used, and inlAss-affibody surface-expressed minicells and control minicells were used as targeting materials to cancer.

The results show that HER2 or EGFR over-expressing cancer cell lines are more uptaked of *Corynebacterium*-derived minicells that surface-expressed affibody or repebody than MDA-MB-435 cancer cell lines. In the case of control minicells, all cancer cell lines apparently did not uptaked (FIG. 6).

EXAMPLE 8

Development of Recombinant Vectors for Drug Protein Expression and Confirming Expression of Drug Protein in *Corynebacterium*

Asparaginase, IL32β, IL32γ, which are drug protein genes, were prepared by PCR (polymerase chain reaction) amplification using corresponding primers listed in Table4. Asparaginase, IL32β, and IL32γ genes were cloned in a pXMJ19 vector by using Hind III and EcoRI restriction enzymes, and finally, pXMJ19/asparaginase, pXMJ19/iI32β, pXMJ19/iI32γ recombinant vectors were prepared. Whether a drug protein is expressed from the gene cloned as described above was confirmed by transforming *Corynebacterium glutamicum* in the same manner as in Example 2. Table 4 shows polynucleotide sequences of primers used to prepare a vector that expresses asparaginase, iI32β, or iI32γ.

TABLE 4

| name | sequence (5' → 3') | restriction enzyme | SEQ ID NO: |
| --- | --- | --- | --- |
| Asp_19 F | CCTAAGCTTATGGAGTTTTTCAAAAAGACGGC | HindIII | 37 |
| Asp_19 R | ACTGAATTCTTAGTACTGATTGAAGATCTGCTGG | EcoRI | 38 |
| il32_19 F | AACAAGCTTATGTGCTTCCCGAAGGTCC | HindIII | 39 |
| il32_19 R | TTTGAATTCTTATTTTGAGGATTGGGGTTCAGAG | EcoRI | 40 |

Whether *Corynebacterium glutamicum* recombinant strains express a drug protein, was confirmed as follows: recombinant strain single colonies cultured in a Chloramphenicol (10 μg/ml)-supplemented LB solid medium were pre-cultured in a 15 ml test tube, and then, 1% thereof was inoculated to a 100 ml flask and cultured at a temperature of 32° C. at a rotational speed of 200 rpm. Thereafter, when the value of OD 600 nm was 0.5, 1 mM IPTG was added to induce protein expression, and the cells were cultured for 3 to 6 hours and collected at certain time intervals. Thereafter, the expression of a drug protein was confirmed by SDS-PAGE assay.

Experimental results show that in the case of the asparaginase protein, a corresponding band appeared on SDS-PAGE, and like in *E. coli*, over-expressed even in *Corynebacterium* (FIG. 7). However, the expression of IL32β and IL32γ on SDS-PAGE was not able to be confirmed. So, His-tag was attached thereto and Western blot analysis was performed. As a result, the expression of IL-32β was confirmed, and the expression of IL-32γ was not able to be confirmed (FIG. 7).

EXAMPLE 9

Confirmation of Over-Expression of Drug Proteins by Applying Ramp-Tag in *Corynebacterium* 1

To design ramp-tag, codon usage of *Corynebacterium glutamicum* (*C. glutamicum* ATCC13032) strain was analyzed, and rare codon was collected. The term 'rare codon' used herein includes a general concept of rare codon and codons that are collected in the following procedure. A translation speed is largely dependent on how quickly amino acid(aa)-tRNA, in which an amino acid is combined, is supplied when translated. Accordingly, when the amount of corresponding amino acid-tRNA is sufficiently great in cells, the translation speed is high; and when the amino acid-tRNA lacks, the translation efficiency may be decreased.

Accordingly, tRNA gene copy may be used as a reference that enables assuming of the concentration of corresponding intracellular tRNA. As known, a conventional codon optimizing method uses a codon frequency. This is because the codon frequency is known to be proportional to corresponding tRNA copy number. In this experiment, a codon frequency (based on 100%) corresponding to each amino acid in *Corynebacterium glutamicum* and a tRNA gene copy (http://gtrnadb.ucsc.edu/) were used, and conditions for collecting a rare codon were understood by referring to the method disclosed in the patent document (KR 10-2014-0112888). Briefly, in each amino acid, a codon pair frequency was 1.0% or lower, and at most 3 codons were collected per an amino acid. Herein, a method in which each codon frequency is taken into consideration, and a method in which a gene copy number of isoacceptor tRNA is taken into consideration were used together (Table 5). Table 5 shows collected rare codons of *Corynebacterium glutamicum* strain.

TABLE 5

| AA | | Codon | Frequency | tRNA |
|---|---|---|---|---|
| <2 Box & Other tRNA Sets> | | | | |
| H | His | CAC | 0.77 | |
| I | Ile | AUA | 0.18 | |
| Y | Tyr | UAU | 0.70 | |
| C | Cys | UGU | 0.20 | |
| | | UGC | 0.41 | |
| <4 Box tRNA Sets> | | | | |
| G | Gly | GGG | 0.67 | 1 |
| P | Pro | CCC | 0.97 | 1 |
| T | Thr | ACG | 0.88 | 1 |
| | | ACA | 0.76 | 1 |
| V | Val | GUA | 0.81 | 1 |
| <6 Box tRNA Sets> | | | | |
| S | Ser | AGU | 0.49 | |
| | | UCG | 0.76 | 1 |
| R | Arg | CGG | 0.49 | 1 |
| | | CGA | 0.66 | |
| | | AGG | 0.32 | 1 |
| | | AGA | 0.22 | 1 |
| L | Leu | CUA | 0.58 | 1 |
| | | UUA | 0.51 | |

A ramp-tag was designed based on a codon frequency shown in the above table, and cloning was performed to fuse the ramp-tag to the N terminus of a target gene. Table 6 shows ramp tag-applied IL32 gene primer sequences in *Corynebacterium glutamicum* strain.

TABLE 6

| name | sequence (5' → 3', ramp-tag) | SEQ ID NO: |
|---|---|---|
| R1-il32b F | GAAACAGAATTAATTGCTATAGCGTGTACTTCGAATCTAATGTGCTTCCCGAAGGTCC | 41 |
| R2-il32b F | GAAACAGAATTAATTAATATAACTTGTCGTAGTCTTTTAATGTGCTTCCCGAAGGTCC | 42 |
| R1-il32g F | GAAACAGAATTAATTAATGTAAACAGTCGTTCGTTGAGGATGTGCTTCCCGAAGGTCC | 43 |
| R2-il32g F | GAAACAGAATTAATTAGCATAAATTGTTTTAGGCGTACTATGTGCTTCCCGAACGTCC | 44 |
| R-il32 R | CAAAACAGCCAAGCTTTATTTTGAGGATTGGGGTTCAGAG | 45 |

In this experiment, ramp-tag applied recombinant drug proteins (IL32β, IL32γ) based on the above logic, were expressed in *Corynebacteria glutamicum*, and an over-expression probability thereof was evaluated. Ramp-tag applied ramp-IL32β and ramp-IL32γ were prepared in the number of two for each, and then, cloned in pXMJ19 vector. ramp-tag applied IL32β and IL32γ genes were amplified by using primers shown in Table 6 by PCR, and cloning was performed by SLIC (sequence ligation independent cloning) using homologous recombination (M Z Li et al., *Nat. Methods.*, 4(3):251-6(2007)). Thereafter, a recombinant vector was used to transform *Corynebacterium glutamicum* as described in Example 2. Then, whether protein expression occurred was confirmed by culturing a recombinant strain and performing SDS-PAGE analysis as described in Example 8. Western blot analysis was performed by using His-tag antibody.

As a result, it was confirmed that in the case of IL32β in *Corynebacterium glutamicum* recombinant strain, compared to a control, a total protein amount of ramp-tag fused IL-32β(R1-IL32β, R2-IL32β) was increased 4.2 to 6.3 fold; and although the control did not express IL32γ at all, when a ramp-tag is applied, over-expression occurred (FIG. 8).

EXAMPLE 10

Confirmation of Auto-Inducible Expression of Quorum Sensing Expression Module-Applied Drug Protein in *Corynebacterium*

This experiment was performed to confirm the functionality of a self-inducing system by quorum sensing in *Corynebacterium glutamicum*, and availability of the quorum sensing as a drug protein expression system. Whether *Vibrio fischeri*, which is Gram-negative bacteria, derived quorum sensing expression system is applicable to *Corynebacterium glutamicum*, was confirmed by identifying how AHL is generated by luxI.

As a result, it was confirmed that Cgl1603 (S-adenosyl methionine synthetase (EC:2.5.1.6)), which is an enzyme for producing SAM (S-adenosylmethionine) used as a substrate for AHL production, was present in *Corynebacterium glutamicum*. On the other hand, whether quorum quenching due to AHL decomposition activity occurs, was confirmed by identifying the presence of AHL hydrolase (hydrolase). Based on amino acid sequence information about *Bacillus*-derived AHL hydrolase, search was performed by using Blast P program of NCBI. Results thereof show that S-adenosyl-homocystein hydrolase (under 25% identities) was identified, and AHL hydrolase-associated enzyme was not identified. Accordingly, regarding *Corynebacterium*, availability of quorum sensing system was provided without adding or deleting a gene in a conventional system.

Whether quorum sensing system is available was confirmed by using mCherry gene as a reporter protein, and asparaginase was expressed as a drug protein and an expression level and activity was confirmed. Constructs were manufactured by using pCES208 as a shuttle vector, and cloning was performed by using a gene that was amplified by using primers shown in Table 7 based on main templates of pBAD24/luxR-luxI-mCherry and pBAD24/luxR-luxI-asparaginase, which are recombinant vectors manufactured according to prior research, and BamHI and EcoRV restriction enzyme sites of pCES208 vector. pBAD24/luxR-luxI-mCherry and pBAD24/luxR-luxI-asparaginase recombinant vectors were manufactured by using luxR and luxI which are known as a *Vibrio fischeri*-derived quorum sensing gene, and by overlapping PCR, a luxRI promoter was included between luxR and luxI, and mcherry or asparaginae gene was located in the downstream of luxI gene, thereby translational coupling. The resultant construct was cloned in pCES208 vector.

Table 7 shows polynucleotide sequences of primers for mCherry and asparaginase quorum sensing expression system.

TABLE 7

| name | sequence (5' → 3') | restriction enzyme | SEQ ID NO: |
|---|---|---|---|
| luxRI F | CCGGGATCCTTAATTTTTAAAGTATGGGC | BamHI | 46 |
| luxRI-mCherry R | TTTGATATCTTACTACTTGTACAGCTCGTC | EcoRV | 47 |
| luxRI-asparaginase R | TTTGATATCTTAGTACTGATTGAAGATCTG | EcoRV | 48 |

The manufactured recombinant vector was used to transform *Corynebacterium glutamicum* as described in Example 2, and selecting was performed in Kanamycin (20 µg/ml)-supplemented LB solid media. Recombinant strain single colonies were pre-cultured in a 15 ml test tube, and then, 1% thereof was inoculated to 100 ml triangular flask and cultured at a temperature of 32° C. and 200 rpm. In the case of *Corynebacterium* recombinant strains transformed with luxR-luxI-mCherry construct, mCherry protein was expressed by quorum sensing mechanism during the culturing without an inducing material. Accordingly, it is confirmed that quorum sensing expression system was functional in *C. glutamicum*. Samples were collected at certain time intervals and SDS-PAGE was performed thereon. As a result, about 10 hours after the culturing, the quorum sensing-caused mCherry protein expression was confirmed (FIG. 9A).

The same experiment was performed using a drug protein-inserted luxR-luxI-asparaginase construct. As a result, it was confirmed that asparaginase was also expressed by quorum sensing expression system (FIG. 9B). Thereafter, a luxR-luxI-asparaginase-transformed *E. coli* recombinant strain and a luxR-luxI-asparaginase-transformed *Corynebacterium glutamicum* recombinant strain were cultured, and then, quorum sensing was performed thereon to induce expression. Then, the cells were collected and lysed by sonication, and activity of asparaginase in the crude state of cells was compared.

As a result, it was confirmed that the two strains showed activity of asparaginase, and the difference in the activity of asparaginase between when expressed in *E. coli* and when expressed in *Corynebacterium glutamicum* was negligible.

EXAMPLE 11

Figure 10:
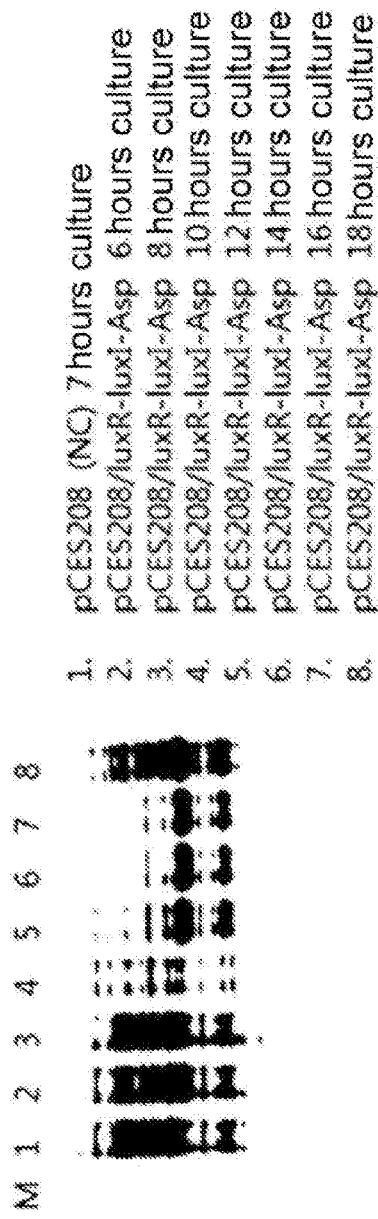
FIG. 10 shows the growth of *Corynebacterium glutamicum* recombinant which is transformed with pCES208/luxR-luxI-asparaginase, and functionality of quorum sensing expression system when co-cultured with animal cells in animal cell culture media. The used animal cell was a breast cancer cell line, MDA-MB-453.

Confirmation of Expression of Drug Proteins when Animal Cells and Recombinant *Corynebacterium* were Cultured Together This experiment was performed to confirm whether a drug protein is normally expressed in an animal cell culture solution when asparaginase gene-inserted recombinant *Corynebacterium glutamicum* and animal cells were co-cultured in same culture medium. Breast cancer cell line MDA-MB-453 was cultured and then treated with trypsin EDTA, and seeded in the number of about $10^4$ cells per each well in a 48 well culture plate and cultured for 20 hours. Separately, when the number of OD 600 nm was 0.5, recombinant *Corynebacterium* cells were collected by centrifugation and suspended in DMEM medium in such a way that each well contains about $10^7$ to $10^8$ cells. The recombinant *Corynebacterium* cells were cultured together with the animal cell. While cultivation, samples were obtained at certain time intervals, and protein expression was confirmed by SDS-PAGE analysis. As a result, it is seen that even when *Corynebacterium glutamicum* transformed with pCES208/luxR-luxI-asparaginase was cultured together with breast cancer cell line MDA-MB-453 in media for culturing animal cells, *Corynebacterium glutamicum* grows well, and by viable cell counting, it was confirmed that the cells proliferate up to the number of $10^9$ that is sufficient to induce self-induction by quorum sensing system. Also, the quorum sensing expression system worked well. This means that asparaginase was over-expressed. Accordingly, it is seen that the construct works well even in-vivo (FIG. 10).

Figure 11:
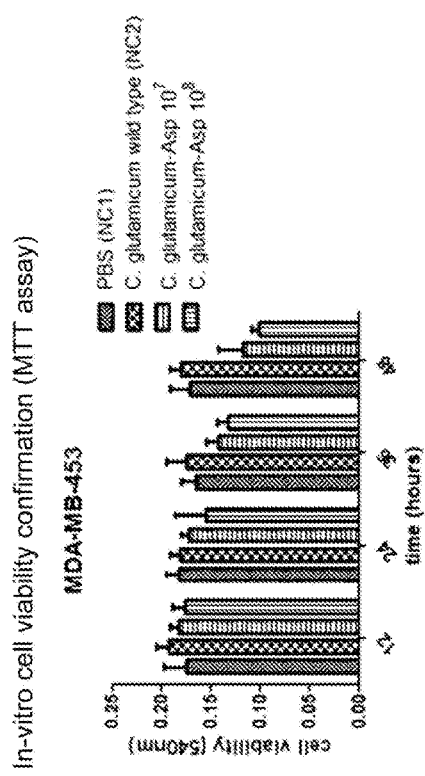
FIG. 11 shows MTT assay results showing cellular activity change of animal cells caused by drug protein asparaginase produced from *Corynebacterium glutamicum* recombinant strain when animal cells were co-cultured with *Corynebacterium glutamicum* recombinant strain as in Example 11.

Thereafter, MTT assay was performed to measure cell activities. Breast cancer cell lines SKBR-3, MDA-MB-453, and MDA-MB-435 were separately cultured, and then, seeded in a 96 well culture plate in the number of about $10^4$ cells per well and cultured overnight at a temperature of 37° C., in a 5% carbon dioxide condition. Thereafter, pCES208/lucR-luxI-asparaginase *Corynebacterium* recombinant strain, which expresses asparaginase by quorum sensing expression system, was added thereto, and then reacted for 4 hours, and washed with PBS, followed by replacing with fresh media and culturing for 24 hours and for 48 hours. Then, the resultant was washed with PBS, and 100 µl of MTT reagent was added thereto, and then reacted at a temperature of 37° C. for 4 hours, and then, 200 µl of DMSO was added thereto, and an absorbance was measured at a wavelength of 570 nm. Results of this experiment show that when treated with the asparaginase-expression recombinant vector transformed in *Corynebacterium*, compared with a control, cellular activity of cancer cells were decreased due to the drug protein, asparaginase (FIG. 11).

EXAMPLE 12

Confirmation of Anti-Cancer Effects of *Corynebacterium*-Derived Drug Delivery System in Cancer Model Animal As a cancer model animal, 6-8 week old Balb/c nude mice (Orient Bio Inc.) were used. All animals used in this experiment was bred, experimented, and euthanized according to a protocol acknowledged by the Animal Research Committee of Chonnam National University and a guide for breeding and using laboratory animals (publication 85-23, Amendment 1985) published by NIH (National Institute of Health). First, subcutaneous tumor was induced in laboratory animals as follows. Breast cancer cells MDA-MB-435 and SKBR-3, which over-express HER2 and EGFR, cultured in Example 10 were harvested by centrifuging, and then suspended in the number of about 1×10⁶ cells in 100 μl of PBS, and the suspended cells were transplanted in thigh subcutaneous tissues of the mice, and the size of cancer tissues was measured (width×length×thickness/2). *Corynebacterium*-derived drug delivery system (*Corynebacterium glutamicum* recombinant strain transformed with pCES208/luxR-luxI-asparaginase) was administered to the mice and experiment was performed.

Anti-cancer effects of *Corynebacterium* derived drug delivery system (*Corynebacteria glutamicum* recombinant strain transformed with pCES208/luxR-luxI-asparaginase) was administered to an animal cancer model prepared as described above by using an asparaginase expression vector-transformed recombinant strain, and the change in the size of cancer tissues was identified. pCES208/luxR-luxI-aspar- agniase recombinant strain was cultured and 5×10⁷ cells thereof were suspended in 100 μl of PBS. The resultant strain was administered to experimental groups, for example, tail veins of three mice with tumor in each of the experimental groups, through a 1 cc insulin syringe. As a control, (1) PBS and (2) pCES208 vector-transformed recombinant strain were separately administered to the mice in the same dose as described above. For the following 20 days, a volumetric change of cancer was measured.

Figure 12:
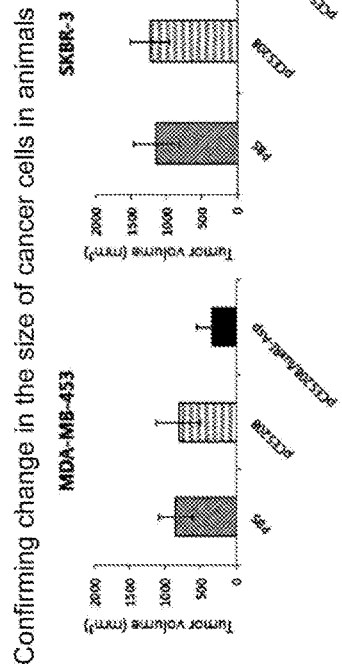
FIG. 12 shows graphs of tumor volume of mice transplanted with breast cancer strains MDA-MB-453, and SKBR-3 when pCES208/luxR-luxI-asparaginase-transformed *Corynebacterium glutamicum* recombinant strain was cultured and administered thereto.

Experimental results show that the asparaginase-mounted recombinant strain leads to the decrease in the size of cancer tissues, compared to the control. Accordingly, it is confirmed that an anti-cancer protein expressed from the *Corynebacterium*-derived drug delivery system (*Corynebacterium glutamicum* recombinant strain transformed with pCES208/luxR-luxI-asparaginase) can treat cancer cells (FIG. 12).

The invention claimed is:

1. A drug delivery system composition, comprising a drug; and a minicell carrying the drug, wherein the minicell is derived from a parA gene-depleted mutant strain of *Corynebacterium* sp. bacteria or a NCgl1366 gene-depleted mutant strain of *Corynebacterium* sp. bacteria, and the *Corynebacterium* sp. bacteria is selected from the group consisting of *Corynebacterium glutamicum, Corynebacterium ammoniagenes, Corynebacterium casei, Corynebacterium efficiens*, and a combination thereof.

2. The drug delivery system composition of claim 1, wherein the drug is an anti-cancer agent.

3. The drug delivery system composition of claim 2, wherein the anti-cancer agent is to inhibit or cure at least one cancer selected from the group consisting of breast cancer, cervical cancer, ovarian cancer, endometrial cancer, melanoma, bladder cancer, lung cancer, pancreatic cancer, colon cancer, prostate cancer, leukemia, acute lymphoblastic leukemia, chronic lymphocytic leukemia, B-cell lymphoma, acute myelogenous leukemia (AML), chronic myelogenous leukemia, thyroid cancer, thyroid follicular cancer, kidney cancer, spleen cancer, craniocervical disorder, gastric cancer, liver cancer, bone cancer, brain cancer, cholangiocarcinoma, small bowel cancer, uterine cancer, and testicular cancer.

4. The drug delivery system composition of claim 2, wherein the anti-cancer agent is at least one anti-cancer agent selected from the group consisting of a chemical preparation, a protein, and a nucleic acid.

5. The drug delivery system composition of claim 4, wherein the anti-cancer agent is the chemical preparation selected from the group consisting of doxorubicin, paclitaxel, docetaxel, cisplatin, carboplatin, oxaliplatin, daunorubicin, epirubicin, idarubicin, valubicin, mitoxantrone, curcumin, gefitinib, erlotinib, irinotecan, topotecan, vinblastine, and vincristine.

6. The drug delivery system composition of claim 4, wherein the anti-cancer agent is the protein selected from the group consisting of an antibody, a transport protein, a structural protein, a regulatory protein, a hormone, a hormone analogue, a cytokine-derived anti-cancer protein, a cytolysis protein, an amino acid lyase, an antiangiogenic factor, a cell adhesion molecule, an enzyme inhibitor, a receptor, a fragment of a receptor, and immunotoxin.

7. The drug delivery system composition of claim 6, wherein the protein is the antibody selected from the group consisting of an immunoglobulin, an antibody fragment, and an antibody analogue.

8. The drug delivery system composition of claim 7, wherein the antibody is the antibody fragment selected from the group consisting of Fab, Fab', F(ab')2, F(ab'), F(ab), Fv, and scFv.

9. The drug delivery system composition of claim 7, wherein the antibody is the antibody analogue selected from the group consisting of affibody, repebody, affilin, DARPin, tetranectin, microbody, peptide aptamer, and avimer.

10. The drug delivery system composition of claim 4, wherein the anti-cancer agent is the nucleic acid selected from the group consisting of siRNA, shRNA, miRNA, antisense RNA, lincRNA, ribozyme, and peptide nucleic acids (PNA).

11. The drug delivery system composition of claim 1, wherein the drug delivery system composition comprises a construct that expresses a protein.

12. The drug delivery system composition of claim 11, wherein the protein comprises (1) an anti-cancer protein, (2) an anti-cancer protein and a cancer cell surface receptor, or (3) an anti-cancer protein and a cancer cell surface antigen.

13. The drug delivery system composition of claim 11, wherein the construct comprises a polynucleotide sequence that encodes a protein linker.

14. The drug delivery system composition of claim 11, wherein the construct comprises a polynucleotide sequence that encodes a ramp tag.

15. An anti-cancer pharmaceutical composition comprising, the drug delivery system composition of claim 1, wherein the drug is a pharmaceutically effective amount of an anti-cancer agent as an active ingredient.

16. The drug delivery system composition of claim 4, wherein the anti-cancer agent comprises an anti-cancer protein and at least one of a cancer cell surface receptor and a cancer cell surface antigen.

* * * * *